ID

US011674965B2

(12) United States Patent
Shieh

(10) Patent No.: US 11,674,965 B2
(45) Date of Patent: Jun. 13, 2023

(54) METHOD FOR PREPARING AND ANALYZING FLUORESCENT COMPOUNDS IN PLASMA

(71) Applicant: MediBeacon, Inc., St. Louis, MO (US)

(72) Inventor: Jeng J. Shieh, Chesterfield, MO (US)

(73) Assignee: MediBeacon Inc., St. Louis, MO (US)

( * ) Notice: Subject to any disclaimer, the term of this patent is extended or adjusted under 35 U.S.C. 154(b) by 762 days.

(21) Appl. No.: 16/192,113

(22) Filed: Nov. 15, 2018

(65) Prior Publication Data
US 2019/0154697 A1    May 23, 2019

Related U.S. Application Data

(60) Provisional application No. 62/588,606, filed on Nov. 20, 2017.

(51) Int. Cl.
| | |
|---|---|
| *G01N 30/06* | (2006.01) |
| *G01N 1/38* | (2006.01) |
| *G01N 33/58* | (2006.01) |
| *G01N 30/14* | (2006.01) |
| *G01N 30/22* | (2006.01) |
| *C07D 229/00* | (2006.01) |

(52) U.S. Cl.
CPC .......... *G01N 33/582* (2013.01); *G01N 30/14* (2013.01); *C07D 229/00* (2013.01); *G01N 1/38* (2013.01); *G01N 30/22* (2013.01); *G01N 2800/347* (2013.01); *Y10T 436/147777* (2015.01)

(58) Field of Classification Search
CPC .. G01N 30/06; G01N 30/14; G01N 2030/146; G01N 2030/047; G01N 2030/884; G01N 1/38; G01N 2001/386; Y10T 436/147777
See application file for complete search history.

(56) References Cited

U.S. PATENT DOCUMENTS

| | | | |
|---|---|---|---|
| 10,101,326 B2 | 10/2018 | Eckhardt | |
| 2003/0236452 A1 | 12/2003 | Melker et al. | |
| 2006/0095102 A1 | 5/2006 | Perez | |
| 2008/0281173 A1 | 11/2008 | Esenaliev et al. | |
| 2009/0076014 A1* | 3/2009 | Oppenheimer | A61K 31/519 514/249 |
| 2013/0116512 A1 | 5/2013 | Imran | |
| 2015/0306486 A1 | 10/2015 | Logan et al. | |

FOREIGN PATENT DOCUMENTS

WO         2016183351 A1    11/2016

OTHER PUBLICATIONS

Farthing, D. et al. "Simple HPLC-UV method for determination of iohexol, iothalamate, p-aminohippuric acid and n-acetyl-p-aminohippuric acid in human plasma and urine with ERPF, GFR and ERPF/GFR ratio determination using colorimetric analysis," Journal of Chromatography B, 826 (2005) 267-272 (Year: 2005).*
Brändström, E. et al. "GFR measurement with iohexol and 51Cr-EDTA. A comparison of the two favoured GFR markers in Europe," Nephrol Dial Transplant (1998) 13: 1176-1182 (Year: 1998).*
Annesley, T.M. et al. "Ultraperformance Liquid Chromatography-Tandem Mass Spectrometry Assay for Iohexol in Human Serum," Clinical Chemistry 55:6 (2009) 1196-1202 (Year: 2009).*
Poreddy, A.R. et al. "Development of fluorescent tracers for the real-time monitoring of renal function," Proc. SPIE 7910, Reporters, Markers, Dyes, Nanoparticles, and Molecular Probes for Biomedical Applications III, 791010 (Feb. 11, 2011) (Year: 2011).*
Koseoglu, M. et al. "Effects of hemolysis interferences on routine biochemistry parameters," Biochemia Medica 2011; 21(1): 79-85 (Year: 2011).*
Seegmiller, J.C. et al. "Iothalamate Quantification by Tandem Mass Spectrometry to Measure Glomerular Filtration Rate," Clinical Chemistry 56:4 (2010) 568-574 (Year: 2010).*
Adiga et al., "Hemolytic index—A tool to measure hemolysis in vitro", Journal of Biotechnology and Biochemistry, 2016, vol. 2, Issue 2, pp. 49-52.
Ardakani et al., "Development and validation of a rapid HPLC-fluorescence method for simultaneous determination of venlafaxine and its major metabolites inhuman plasma", DARU, 2010, vol. 18, No. 2, pp. 97-102.
Huang et al., "High-Performance Liquid Chromatographic-Fluorescent Method to Determine Chloroacetaldehyde, a Neurotoxic Metabolite of the Anticancer Drug Ifosfamide, in Plasma and in Liver Microsomal Incubations", Analytical Biochemistry, 1999, vol. 273, pp. 117-125.
Kang et al., "Overview of Therapeutic Drug Monitoring", The Korean Journal of Internal Medicine, Mar. 2009, vol. 24, No. 1, pp. 1-10.
Koseoglu et al., "Effects of hemolysis interference on routine biochemistry parameters", Biochemia Medica, 2011, vol. 21, No. 1., pp. 79-85.
Rajagopalan et al., "Hydrophilic Pyrazine Dyes as Exogenous Fluorescent Tracer Agents for Real-Time Point-of-Care Measurement of Glomerular Filtration Rate", J Med. Chem., 2011, vol. 54, pp. 5048-5058.
International Search Report and Written Opinion for PCT/US18/61282, dated Feb. 4, 2019, 9 pages.
Brenner et al., "Quantitative Importance of Changes in Postglomerular Colloid Osmotic Pressure in Mediating Glomerulotubular Balance in the Rat," The Journal of Clinical Investigation, vol. 52, (1973), pp. 190-197.
Chinen et al., "Fluorescence-Enhanced Europium-Diethylenetriaminepentaacetic (DTPA)-Monoamide Complexes for the Assessment of Renal Function," J. Med. Chem., vol. 51, (2008), pp. 957-962.

(Continued)

*Primary Examiner* — Jennifer Wecker
*Assistant Examiner* — Michelle Adams
(74) *Attorney, Agent, or Firm* — Armstrong Teasdale LLP

(57) ABSTRACT

Disclosed herein is a method for analyzing the concentration of a fluorescent compound in the plasma of a patient. The method includes collecting a sample of plasma from a patient, diluting the sample with a solvent and analyzing the diluted sample by HPLC. The sample does not need to be dried down during sample preparation nor is an internal standard required.

23 Claims, 15 Drawing Sheets

(56) References Cited

OTHER PUBLICATIONS

Dean et al., "Inulin, Diodone, Creatinine And Urea Clearances In Newborn Infants," J. Physiol., vol. 106, (1947), pp. 431-439.

Debreczeny et al., "Transdermal Optical Renal Function Monitoring in Humans: Development, Verification, and Validation of a Prototype Device," Journal of Biomedical Optics, vol. 23, No. 5, (May 2018), 057003-1-057003-9.

Friedman et al., "A comparison of the renal clearances of allantoin and inulin in man," Fed. Proc., vol. 7, No. 1 Pt 1, (1948), 1 page.

Gregory et al., "Studies on Hypertension; Effect of Lowering the Blood Pressures of Hypertensive Patients by High Spinal Anesthesia on the Renal Function as Measured by Inulin and Diodrast Clearances," Arch. Intern. Med. (Chic), vol. 77, (1946), pp. 385-392.

Levin et al., "The Effect of Chronic Anemia on Renal Function as Measured by Inulin and Diodrast Clearances," Proc. Annu. Meet. Cent. Soc. Clin. Res. U. S., vol. 20, (1947), 3 pages.

Nagpal et al., "Combined Fluorescein, Indocyanine angiography and Optical Coherent Tomography Using Spectralis," Rajasthan Journal Of Ophthalmology, (2011), 8 pages.

Navar et al., "Distal Tubular Feedback in the Autoregulation of Single Nephron Glomerular Filtration Rate," J. Clin. Invest., vol. 53, (1974), pp. 516-525.

Nicholson et al., "Renal Function as Affected by Experimental Unilateral Kidney Lesions: I. Nephrosis Due to Sodium Rartrate," J. Exp. Med., Vil 68, (1938), pp. 439-456.

Pill et al., "Fluorescein-labeled Sinistrin as Marker of Glomerular Filtration Rate," European Journal of Medicinal Chemistry, vol. 40, (2005), pp. 1056-1061.

Poujeol et al., "Glomerular Filtration Rate and Microsphere Distributions in Single Nephron of Rat Kidney," Pflugers Arch., vol. 357, (1975), pp. 291-301.

Robson et al., "The Determination of the Renal Clearance of Inulin in Man," Q. J. Exp. Physiol., vol. 35, (1949), pp. 111-134.

Schock-Kusch et al., "Transcutaneous measurement of glomerular filtration rate using FITC-sinistrin in rats," Nephrol Dial Transplant, vol. 24, (2009), pp. 2997-3001.

Shannon et al., "The Renal Excretion of Inulin and Creatinine by the Anaesthetized Dog and the Pump-Lung-Kidney Preparation", J. Physiol., vol. 98, (1940), pp. 97-108.

Yu et al., "Rapid determination of renal filtration function using an optical ratiometric imaging approach," Am. J. Physiol. Renal. Physiol., vol. 292, (2007), pp. F1873-F1880.

International Search Report received for PCT Patent Application No. PCT/US2019/013784, dated May 7, 2019, 3 pages.

International Preliminary Report on Patentability received for PCT Patent Application No. PCT/US2019/013784, dated Jul. 30, 2020, 8 pages.

Debreczeny et al., "Development and clinical trial results of a prototype device for trans-cutaneous monitoring of kidney function", Progress in Biomedical Optics and Imaging, SPIE—International Society for Optical Engineering, Bellingham, WA, US, vol. 10079, Feb. 21, 2017, pp. 100790K-100790K.

Dorshow et al., "New optical probes for the continuous monitoring of renal function", SPIE, Feb. 22, 2008, vol. 6867, 11 pages.

Hubbard et al., "Application of a highly specific and sensitive fluorescent HPLC method for topotecan lactone in whole blood", Biomedical Chromatography, vol. 23, No. 7, Jul. 1, 2009, pp. 707-713.

Supplementary European Search Report for EP 18 87 9660, dated Jul. 16, 2021, 9 pages.

Garcia et al., "Determination of Lomefloxacin in Plasma Samples by HPLC with Fluorescence Detection. Application to Pharmacokinetic Studies", Chromatographia, vol. 54, Dec. 31, 2001, pp. 577-580.

\* cited by examiner

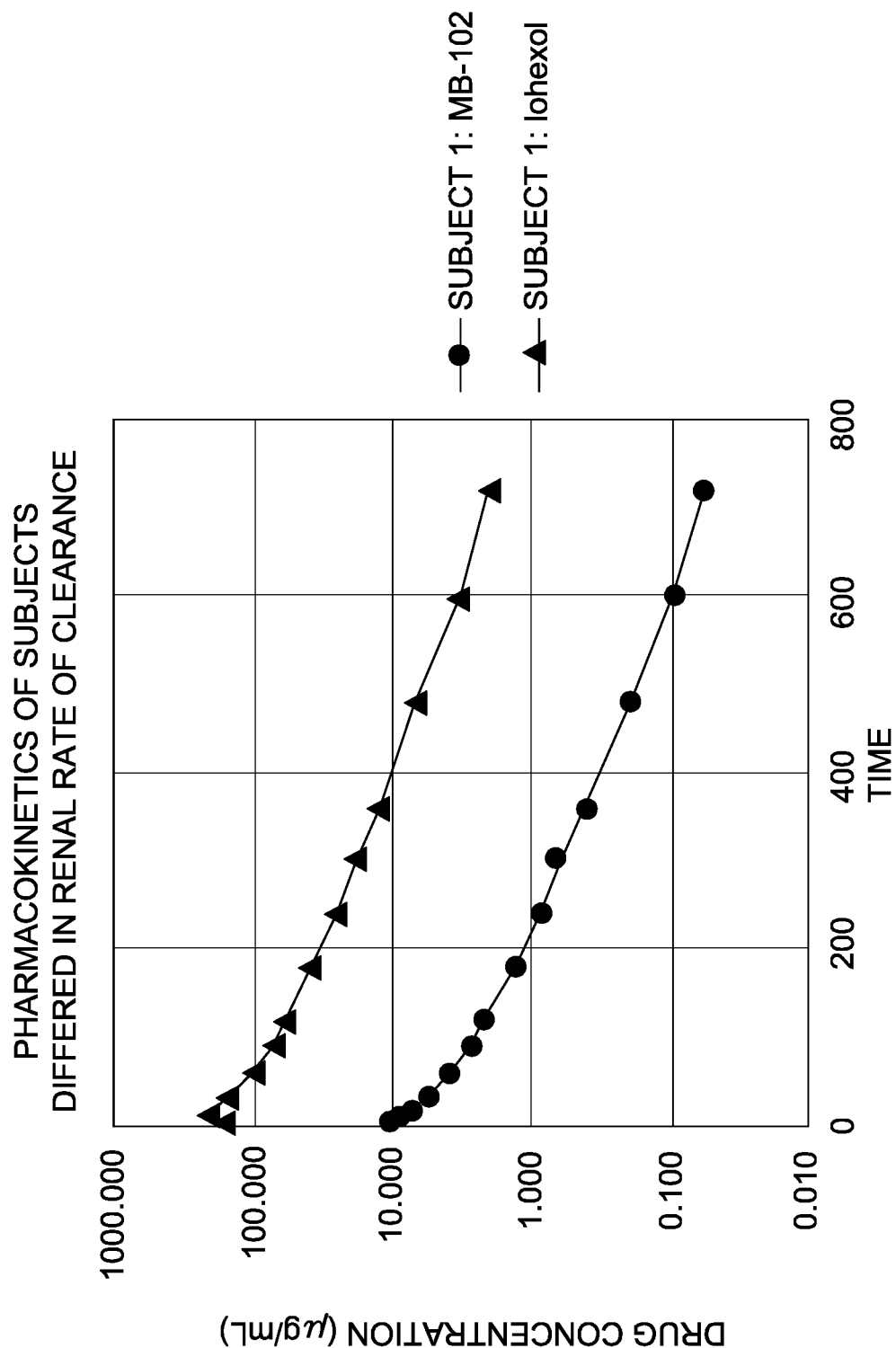

METHOD FOR PREPARING AND ANALYZING FLUORESCENT COMPOUNDS IN PLASMA

CROSS REFERENCE TO RELATED APPLICATIONS

This application claims priority benefit of U.S. Provisional Application Ser. No. 62/588,606 filed Nov. 20, 2017, the entire contents of which is incorporated by reference.

BACKGROUND OF THE INVENTION

The field of the invention relates generally to the detection and quantification of a fluorescent compound in plasma. More specifically, the application relates to methods for analyzing and quantifying (2R,2'R)-2,2'-((3,6-diaminopyrazine-2,5-dicarbonyl)bis(azanediyl))bis(3-hydroxypropanoic acid) in the plasma of a patient.

The analysis of small molecule pharmaceuticals in the plasma of a patient is frequently required both during and after clinical trials. During clinical trials, it is necessary to establish the correct dose of a drug in order to optimize efficacy and minimize adverse side effects. In some instances, too little drug (i.e., minimal efficacy and therapeutic effect) can be as detrimental as too much (i.e., adverse side effects).

The renal glomerular filtration rate (GFR) is widely accepted as the most reliable measure of renal function in a patient. As such, there is a medical need for an accurate real-time measurement of GFR to assess kidney function due to either acute or chronic kidney impairment. The current common clinical practice in assessing kidney function measures the serum creatinine level and its 24 hour clearance rate to obtain an estimated GFR (eGFR) based on the GFR equations of Ferguson and Waikar or Inker, et al. However this methodology lacks appropriate sensitivity and accuracy while being time-delayed because of the time necessary for a suitable laboratory to process the samples. Additionally, the results vary significantly depending on factors such as age, hydration, muscle mass, and diet, etc.

Exogenous GFR tracer agents, such as iohexol (Omnipaque®), shown in FIG. 1, provide a valid GFR assessment. Iohexol is not metabolized or pooled in patient organs. Its distribution follows a simple concentration gradient across capillaries and is entirely eliminated by simple glomerular filtration without tubular renal secretion or reabsorption. In order to use iohexol for GFR determination, blood samples are collected from a patient at multiple time points followed by careful laboratory analysis. The GFR value is determined via PK analysis of the data using WinNonlin PK/PD Modeling and Simulation Software. This is a labor intensive process which places significant demands on medical and laboratory personnel. It also takes an increased amount of time because multiple samples must be collected over several hours in addition to the laboratory analysis required afterward.

Chronic Kidney Disease (CKD) is a medical condition characterized in the gradual loss of kidney function over time. It includes conditions that damage the kidneys and decrease their ability to properly remove waste products from the bloodstream of an individual. Complications from CKD include high blood pressure, anemia (low blood count), weak bones, poor nutritional health, nerve damage and an increased risk of heart disease. According to the National Kidney Foundation, approximately two-thirds of all cases of CKD are caused by diabetes or hypertension. In addition to family history, other risk factors for kidney disease include age, ethnicity, hypertension, and diabetes. The GFR is the best test to determine the level of kidney function and assess the stage of a patient's CKD.

The GFR is an important test to determine the level of kidney function which determines the stage of CKD. As shown below, the lower the GFR in a patient, the more serious the CKD.

| Stage | Description | GFR |
|---|---|---|
| At increased risk | Increase of risk factors (e.g., diabetes, high blood pressure, family history, age, ethnicity) | >90 |
| 1 | Kidney damage with normal kidney function | >90 |
| 2 | Kidney damage with mild loss of kidney function | 60-89 |
| 3a | Mild to moderate loss of kidney function | 44-59 |
| 3b | Moderate to severe loss of kidney function | 30-43 |
| 4 | Severe loss of kidney function | 15-29 |
| 5 | Kidney failure; dialysis required | <15 |

Much effort has been directed at finding exogenous fluorescent agents that can be detected transdermally in real time. See U.S. Pat. Nos. 9,480,687, 9,114,160, 8,722,685, 8,115,000, and 8,778,309 for their teachings thereof; each of which is incorporated by reference herein in their entirety. MB-102, a fluorescent compound that exhibits excellent photo-physical properties and other chemical and physical characteristics, has been synthesized in addition to many other small molecules.

MB-102, (2R,2'R)-2,2'-((3,6-diaminopyrazine-2,5-dicarbonyl)bis(azanediyl)) bis(3-hydroxypropanoic acid), shown in FIG. 1, is a fluorescent agent under development for real time GFR determination. It emits a strong fluorescent signal at 556 nm when excited 434 nm and is currently in a human clinical study. Significantly, the amount of MB-102 circulating in the bloodstream of a patient and the rate in which it is eliminated by renal filtration can be measured transdermally in real time. This eliminates the need for time consuming sample collection and laboratory analysis while providing medical personnel with a real time assessment of kidney function in a patient. As such, a need exists to validate the accuracy of methods used to quantify the amount of MB-102 in the plasma or bloodstream of a patient.

Laboratory analysis of plasma samples often involves protein precipitation, evaporation and drying, followed by reconstitution in a solvent compatible with HPLC. This is a labor intensive process and extends the time required before results are obtained. Another drawback to protein precipitation methods is the need for an internal standard in a sample to ensure accurate results. These steps lengthen the time required for analysis and introduce opportunities for error. Thus a need exists to both shorten the time required for analysis and reduce the opportunities for error.

BRIEF DESCRIPTION OF THE INVENTION

In one aspect, disclosed herein is a method for measuring the amount of a fluorescent compound in plasma. The method includes collecting a sample of plasma, diluting the sample of plasma with at least one solvent, and analyzing the diluted sample by HPLC thereby measuring the amount of the compound in the plasma. The sample of plasma is not dried before HPLC analysis, and no internal standard is added to the sample.

In another aspect, disclosed herein is a method for measuring the amount of a fluorescent compound in plasma. The method includes collecting a sample of plasma from a patient, adding to the sample at least one solvent thereby causing plasma proteins to precipitate, removing the precipitated plasma proteins from the sample, and analyzing the sample by HPLC thereby measuring the amount of the compound in the plasma. The sample is not dried before HPLC analysis, and no internal standard is added to the sample.

BRIEF DESCRIPTION OF THE DRAWINGS

FIGS. 8a, 8b and 8c are graphs comparing the clearance rates of MB-102 and iohexol for three patients in the clinical trials.

DETAILED DESCRIPTION OF THE INVENTION

Figure 1:
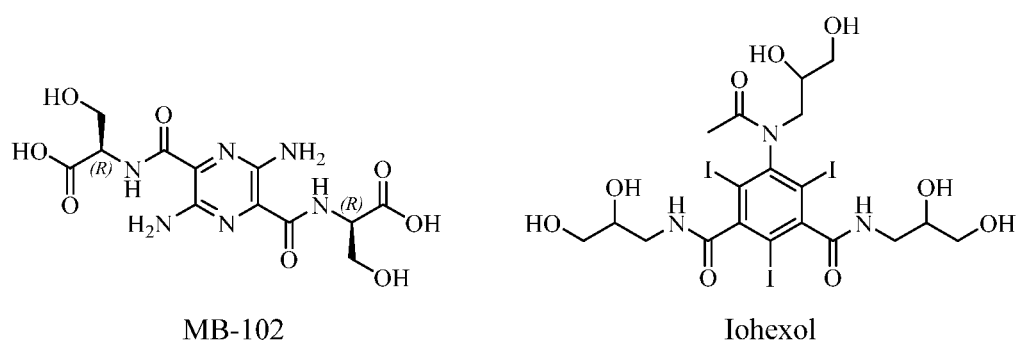
FIG. 1 illustrates the structures of MB-102 and iohexol.

Disclosed herein is a method for monitoring the concentration of a fluorescent compound in a patient in need thereof. The method comprises collecting a sample of plasma, diluting the sample of plasma with at least one solvent, and analyzing the diluted sample by high pressure liquid chromatography (HPLC). Importantly, the sample has not been dried before analysis nor has an internal standard been added during sample preparation.

In some embodiments the fluorescent compound is a compound of Formula I as disclosed elsewhere herein. Preferably the compound is (2R,2'R)-2,2'-((3,6-diaminopyrazine-2,5-dicarbonyl)bis(azanediyl))bis(3-hydroxypropanoic acid) (MB-102), or a pharmaceutically acceptable salt thereof, shown below:

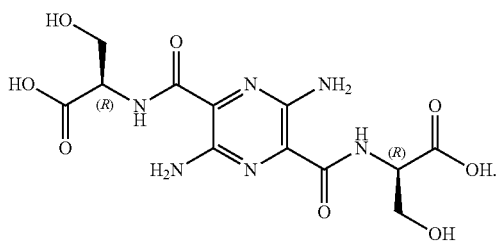

In some embodiments the plasma sample is prepared by collecting a blood sample from a patient, and the plasma is collected using methods known in the art. The plasma can be collected from a human patient, from an animal, or from an in vitro study. Examples of animals from which the plasma may be collected include, but are not limited to, dogs, cats, cows, horses, pigs, goats, monkeys, rats and mice. Preferably, the plasma is collected from a human patient. The plasma may be analyzed immediately for the fluorescent compound or it may be stored for analysis at later period in time. If the sample of plasma is stored for analysis at a later period in time, sample storage is done to minimize decomposition. One method of storage is to freeze the sample at a temperature of −80° C. or lower. Other storage methods as recognized in the art that prevent sample degradation are acceptable and encompassed herein.

Before HPLC analysis, the sample is diluted with at least one solvent. The solvent can be aqueous or organic. In some aspects, the aqueous solvent is saline. In some aspects more than one solvent will be used. Each of the solvents may be aqueous or non-aqueous and is selected independently of the other.

In some aspects, the aqueous solvent is in the form of a buffer selected from the group consisting of phosphate, acetate, bicarbonate, carbonate, formate, gluconate, lactate, citrate, sulfonate, ammonium, guanidinium, HEPES, cacodylate, Tris, tris-HCl, maleate, borate, glycinate, succinate, PIPES and any combination thereof. Preferably, the aqueous solvent is phosphate buffered saline (PBS).

Suitable non-aqueous solvents include, but are not limited to, methanol, ethanol, ethylene glycol, ethyl acetate, hexane, chloroform, DMF, DMSO, acetic acid, acetone, acetonitrile, butanol, carbon tetrachloride, diethylene glycol, diethyl ether, DME, ethylene glycol, methylene chloride, nitromethane, petroleum ether, propanol, pyridine, toluene, MTBE, triethylamine, xylene, and benzene. Preferably, the organic solvent is miscible with water. Most preferably, the organic solvent is methanol, ethanol, acetonitrile or DMSO. In one embodiment, the organic solvent is methanol.

The pH of the buffer will be compatible with the HPLC solvent system and will not cause decomposition of the plasma sample within the time period necessary to conduct the HPLC analysis. In some aspects, the pH will be between from about 2 to 12. In yet another aspect, the pH of the aqueous solvent will be about 2, about 3, about 4, about 5, about 6, about 7, about 8, about 9, about 10, about 11, or about 12. As used in this context, "about" in reference to pH means±0.5 units. In yet another aspect, the pH of the aqueous sample is about physiological pH, approximately between 7.0 and 7.4.

Dilution of the plasma sample with the solvent will be done such that the concentration of the fluorescent compound in the plasma is readily analyzed by HPLC. As is known in the art, if the concentration of the analyte it too high it can overload the column and the detector. This can lead to peak tailing and changes in the retention times of the analytes which can lead to errors in quantification and identification. If the concentration of the analyte is too low, the signal can be lost in the baseline noise and not detected properly. Either situation must be avoided in order for the methods disclosed herein to provide accurate results. It is not uncommon for a sample to be analyzed only to determine that the concentration of the analytes is too high. In such cases, the sample is diluted again and reanalyzed. In some aspects, the plasma sample is diluted with solvent in a 1:1 v/v ratio (sample:solvent). In yet another aspect the dilution ratio is from 1:(0.1-100) v/v. In still yet another aspect, the dilution ratio is from (0.1-100):1 v/v. In still yet another aspect, the dilution ratio (v/v) is from 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, 1:50, 1:60, 1:70, 1:80, 1:90, 1:100, 1:200, 1:300, 1:400, 1:500, 1:600, 1:700, 1:800, 1:900, or 1:1000.

In yet another aspect of the method for measuring the concentration of a fluorescent compound in the plasma of a patient disclosed herein, the method comprises collecting a sample of plasma from a patient, adding at least one solvent to the sample to cause the proteins to precipitate, removing the precipitated proteins from the sample, and analyzing the sample by HPLC. Importantly, the sample has not been dried before analysis nor has an internal standard been added during sample preparation.

The fluorescent compound may be a fluorescent dye. The fluorescent dyes of the present disclosure tend to have absorption, excitation, and emission wavelengths that are all within the near-infrared (NIR) or visible spectrum of about 350 nm or greater. This is beneficial for diagnostic procedures since visible and NIR light are not likely to damage tissue. Light having a wavelength of about 350 nm or greater tends to penetrate into tissues thereby permitting diagnostic procedures to be conducted in tissues of interest that may not be reachable using UV wavelengths that are less than about 350 nm. Suitable fluorescent dyes include acridines, acridones, anthracenes, anthracylines, anthraquinones, aza azulenes, azo azulenes, benzenes, benzimidazoles, benzofurans, benzoindocarbocyanines, benzoindoles, benzothiophenes, carbazoles, coumarins, cyanines, dibenzofurans, dibenzothiophenes, dipyrrolo dyes, flavones, fluoresceins, imidazoles, indocarbocyanines, indocyanines, indoles, isoindoles, isoquinolines, naphthacenediones, naphthalenes, naphthoquinones, phenanthrenes, phenanthridines, phenanthridines, phenoselenazines, phenothiazines, phenoxazines, phenylxanthenes, polyfluorobenzenes, purines, pyrazines, pyrazoles, pyridines, pyrimidones, pyrroles, quantum dots, quinolines, quinolones, rhodamines, squaraines, tetracenes, thiophenes, triphenyl methane dyes, xanthenes, xanthones, and derivatives thereof.

In some embodiments, the fluorescent compound is a compound of Formula I as disclosed elsewhere herein. Preferably the compound is (2R,2'R)-2,2'-((3,6-diaminopyrazine-2,5-dicarbonyl)bis(azanediyl))bis(3-hydroxypropanoic acid) ("MB-102"), or a pharmaceutically acceptable salt thereof, shown below:

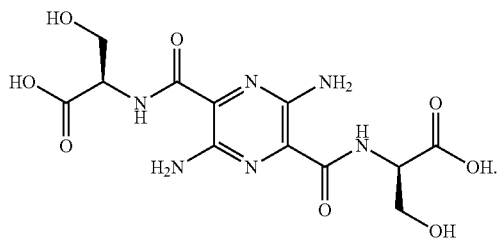 [SMILES: Nc1nc(C(=O)N[C@H](CO)C(=O)O)c(N)nc1C(=O)N[C@H](CO)C(=O)O]

In some embodiments the plasma sample is prepared by collecting a blood sample from a patient, and the plasma is isolated using methods known in the art. The plasma may be analyzed immediately for the fluorescent compound or it may be stored for analysis at another time. If the sample of plasma is stored for analysis at a later period in time, sample storage will be done to minimize decomposition and breakdown. One method of storage is to freeze the sample at a temperature of −80° C. or lower. Other storage methods as recognized in the art that prevent sample degradation are acceptable and encompassed herein.

In some embodiments the solvent added to cause protein precipitation is an organic solvent selected from the group consisting of methanol, ethanol, ethylene glycol, ethyl acetate, hexane, chloroform, DMF, DMSO, acetic acid, acetone, acetonitrile, butanol, carbon tetrachloride, diethylene glycol, diethyl ether, DME, ethylene glycol, methylene chloride, nitromethane, petroleum ether, propanol, pyridine, toluene, MTBE, triethylamine, xylene, and benzene. In some aspects more than one solvent is used. Each of the solvents may be aqueous or non-aqueous and is selected independently of the other.

Removal of the precipitated proteins is done using methods known in the art. Filtration and centrifugation are two methods encompassed herein.

After removal of the precipitated proteins, the sample is analyzed directly or it may be diluted with an additional solvent. The solvent used for the dilution may be aqueous, non-aqueous or any combination thereof. In some embodiments, the aqueous solvent is saline. In yet another aspect, the aqueous solvent is a buffer selected from the group consisting of phosphate, acetate, bicarbonate, carbonate, formate, gluconate, lactate, citrate, sulfonate, ammonium, guanidinium, HEPES, cacodylate, Tris, tris-HCl, maleate, borate, glycinate, succinate, PIPES and any combination thereof. Preferably, the aqueous solvent is phosphate buffered saline.

The pH of the aqueous solvent system will be compatible with the HPLC solvent system and will not cause decomposition of the plasma sample with the time necessary to conduct the HPLC analysis. In some aspects, the pH will be between from about 2 to 12. In yet another aspect, the pH of the aqueous solvent will be about 2, about 3, about 4, about 5, about 6, about 7, about 8, about 9, about 10, about 11, or about 12. As used in this context, "about" in reference to pH means ±0.5 units. In yet another aspect, the pH of the aqueous sample is about physiological pH, between 7.0 and 7.4.

In yet another aspect, the solvent used to dilute the sample before analysis is an organic, non-aqueous solvent. Suitable organic, non-aqueous solvents include, but are not limited to, methanol, ethanol, ethylene glycol, ethyl acetate, hexane, chloroform, DMF, DMSO, acetic acid, acetone, acetonitrile, butanol, carbon tetrachloride, diethylene glycol, diethyl ether, DME, ethylene glycol, methylene chloride, nitromethane, petroleum ether, propanol, pyridine, toluene, MTBE, triethylamine, xylene, and benzene. Preferably, the organic solvent is miscible with water. Most preferably, the organic solvent is methanol, ethanol, acetonitrile or DMSO. In one embodiment, the organic solvent is methanol.

In still yet another aspect, the solvent used to dilute the sample includes at least two different solvents selected from any possible combinations of the aqueous and organic solvents disclosed herein. Additionally, because HPLC is used for the analysis, the solvent system is selected such that it does not interfere with analyte detection.

The amount of solvent used to precipitate the proteins and/or prepare the sample for HPLC analysis will vary depending on the sample. As discussed elsewhere herein, the amount of solvent necessary will be adjusted such that the HPLC provides proper results. Two dilutions may occur with this method: a) solvent addition to cause protein precipitation, and b) solvent addition to the supernatant after removal of the protein precipitate. In this method, the combined amount of solvent added for these two steps will affect the concentration of the analyte in the HPLC analysis. The combined amount of solvent added to the plasma sample will be such that the analyte concentration is not too high or too low. In some aspects, the plasma sample is diluted with solvent in a 1:1 v/v ratio (sample:solvent) where this refers to the ratio of the sample to the combined volume of the solvents in both dilutions. In yet another aspect the dilution ratio is from 1:(0.1-100) v/v. In still yet another aspect, the dilution ratio is from (0.1-100):1 v/v. In still yet another aspect, the dilution ratio (v/v) is from 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, 1:50, 1:60, 1:70, 1:80, 1:90, 1:100, 1:200, 1:300, 1:400, 1:500, 1:600, 1:700, 1:800, 1:900, or 1:1000. The ratio of the solvents used in the two dilutions can be from (0.1-100):(100-0.1) v/v relative to each other. In some aspects, only the dilution step for protein precipitation may occur. The concentration of the sample after protein precipitation may be such that no further dilution is required.

As is known in the art, blood hemolysis can be a problem when blood samples are collected from a patient. There are many causes of blood hemolysis, including difficult specimen collection, unsecure lines, contamination, improper needle size, improper tube mixing, incorrectly filled sample tubes and sample storage. Any blood hemolysis in a collected sample can interfere with an analysis performed on plasma. Hemolysis is known to cause inaccurate laboratory test results in many different types of analysis due to contamination of the plasma with the contents of the hemolyzed red blood cells. After hemolysis, hemoglobin is released into the plasma or serum of the sample. One common sign of hemolysis is a color change in the plasma or serum of a patient. A rough estimate of the amount of hemoglobin in plasma or serum, thus the presence or absence of hemolysis, can be done visually using a color chart found at: http://blog.fisherbioservices.com/avoiding-hemolysis-in-blood-sample-collection-and-processing, which is incorporated by reference for its teaching thereof. Another sign of hemolysis is a decrease in the cloudiness of a blood sample due a decrease in red blood cells that cause light scattering.

In some aspects, the methods for measuring the concentration of a fluorescent compound in the plasma of a patient are applied to a sample where at least some hemolysis has occurred. In yet another aspect, the methods for measuring the concentration of MB-102 in the plasma of a patient are applied to plasma samples where partial or complete hemolysis has occurred.

In some embodiments disclosed herein, the fluorescent compound is a pyrazine molecule of Formula I, or a pharmaceutically acceptable salt thereof, wherein

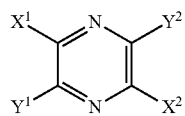

Formula I each of $X^1$ and $X^2$ is independently —$CO_2R^1$, —$CONR^1R^2$, —CO(AA) or —CONH(PS); each of $Y^1$ and $Y^2$ is independently selected from the group consisting of —$NR^1R^2$ and

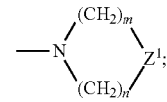

$Z^1$ is a single bond, —$CR^1R^2$—, —O—, —$NR^1$—, —$NCOR^1$—, —S—, —SO—, or —$SO_2$—; each of $R^1$ to $R^2$ are independently selected from the group consisting of H, —$CH_2(CHOH)_aH$, —$CH_2(CHOH)_aCH_3$, —$CH_2(CHOH)_aCO_2H$, —$(CHCO_2H)_aCO_2H$, —$(CH_2CH_2O)_cH$, —$(CH_2CH_2O)CH_3$, —$(CH_2)_aSO_3H$, —$(CH_2)_aSO_3^-$, —$(CH_2)_aSO_2H$, —$(CH_2)_aSO_2^-$, —$(CH_2)_aNHSO_3H$, —$(CH_2)_aNHSO_3^-$, —$(CH_2)_aNHSO_2H$, —$(CH_2)_aNHSO_2^-$, —$(CH_2)_aPO_4H_3$, —$(CH_2)_aPO_4H_2^-$, —$(CH_2)_aPO_4H^{2-}$, —$(CH_2)_aPO_4^{3-}$, —$(CH_2)_aPO_3H_2$, —$(CH_2)_aPO_3H^-$, and —$(CH_2)_aPO_3^{2-}$; AA is a peptide chain comprising one or more amino acids selected from the group consisting of natural and unnatural amino acids, linked together by peptide or amide bonds and each instance of AA may be the same or different than each other instance; PS is a sulfated or non-sulfated polysaccharide chain comprising one or more monosaccharide units connected by glycosidic linkages; and 'a' is a number from 1 to 10, 'c' is a number from 1 to 100, and each of 'm' and 'n' are independently a number from 1 to 3. In some aspects, at least one of $X^1$ and $X^2$ is —CO(PS) or —CO(AA). In yet another aspect, both $X^1$ and $X^2$ are —CO(AA).

(AA) is a peptide chain comprising one or more natural or unnatural amino acids linked together by peptide bonds. The peptide chain (AA) may be a single amino acid, a homopolypeptide chain or a heteropolypeptide chain, and may be any appropriate length. In some embodiments, the natural or unnatural amino acid is an α-amino acid. In yet another aspect, the α-amino acid is a D-α-amino acid or an L-α-amino acid. In a polypeptide chain comprising two or more amino acids, each amino acid is selected independently of the other(s) in all aspects, including, but not limited to, the structure of the side chain and the stereochemistry. For example, in some embodiments, the peptide chain may include 1 to 100 amino acid(s), 1 to 90 amino acid(s), 1 to 80 amino acid(s), 1 to 70 amino acid(s), 1 to 60 amino acid(s), 1 to 50 amino acid(s), 1 to 40 amino acid(s), 1 to 30 amino acid(s), 1 to 20 amino acid(s), or even 1 to 10 amino acid(s). In some embodiments, the peptide chain may include 1 to 100 α-amino acid(s), 1 to 90 α-amino acid(s), 1 to 80 α-amino acid(s), 1 to 70 α-amino acid(s), 1 to 60 α-amino acid(s), 1 to 50 α-amino acid(s), 1 to 40 α-amino acid(s), 1 to 30 α-amino acid(s), 1 to 20 α-amino acid(s), or even 1 to 10 α-amino acid(s). In some embodiments, the amino acid is selected from the group consisting of D-alanine, D-arginine D-asparagine, D-aspartic acid, D-cysteine, D-glutamic acid, D-glutamine, glycine, D-histidine, D-homoserine, D-isoleucine, D-leucine, D-lysine, D-methionine, D-phenylalanine, D-proline, D-serine, D-threonine, D-tyrosine, D-tryptophan, and D-valine. In some embodiments, the α-amino acids of the peptide chain (AA) are selected from the group consisting of arginine, asparagine, aspartic acid, glutamine, glutamic acid, histidine, homoserine, lysine, and serine. In some embodiments, the α-amino acids of the peptide chain (AA) are selected from the group consisting of aspartic acid, glutamic acid, homoserine, and serine. In some embodiments, the peptide chain (AA) refers to a single amino (e.g., D-aspartic acid or D-serine).

In some embodiments, (AA) is a single amino acid selected from the group consisting of the 21 essential amino acids. In other aspects, AA is selected from the group consisting of D-arginine, D-asparagine, D-aspartic acid, D-glutamine, D-glutamic acid, D-histidine, D-homoserine, D-lysine, and D-serine. Preferably, AA is D-aspartic acid, glycine, D-serine, or D-tyrosine. Most preferably, AA is D-serine.

In some embodiments, (AA) is a β-amino acid. Examples of β-amino acids include, but are not limited to, β-phenylalanine, β-alanine, 3-amino-3-(3-bromophenyl)propionic acid, 3-aminobutanoic acid, cis-2-amino-3-cyclopentene-1-carboxylic acid, trans-2-amino-3-cyclopentene-1-carboxylic acid, 3-aminoisobutyric acid, 3-amino-2-phenylpropionic acid, 3-amino-4-(4-biphenylyl)butyric acid, cis-3-amino-cyclohexanecarboxylic acid, trans-3-amino-cyclohexanecarboxylic acid, 3amino-cyclopentanecarboxylic acid, 3-amino-2-hydroxy-4-phenylbutyric acid, 2-(aminomethyl)phenylacetic acid, 3-amino-2-methylpropionic acid, 3-amino-4-(2-naphthyl)butyric acid, 3-amino-5-phenylpentanoic acid, 3-amino-2-phenylpropionic acid, 4-bromo-β-Phe-OH, 4-chloro-β-Homophe-OH, 4-chloro-β-Phe-OH, 2-cyano-β-Homophe-OH, 2-cyano-β-Homophe-OH, 4-cyano-β-Homophe-OH, 3-cyano-β-Phe-OH, 4-cyano-β-Phe-OH, 3,4-dimethoxy-β-Phe-OH, γ,γ-diphenyβ-Homoala-OH, 4-fluoro-β-Phe-OH, β-Gln-OH, β-Homoala-OH, β-Homoarg-OH, β-Homogln-OH, β-Homoglu-OH, β-Homohyp-OH, β-Homoleu-OH, β-Homolys-OH, β-Homomet-OH, β2-homophenylalanine, β-Homophe-OH, β3-Homopro-OH, β-Homoser-OH, β-Homothr-OH, β-Homotrp-OH, β-Homotrp-OMe, β-Homotyr-OH, β-Leu-OH, β-Leu-OH, β-Lys(Z)—OH, 3-methoxy-β-Phe-OH, 3-methoxy-β-Phe-OH, 4-methoxy-β-Phe-OH, 4-methy-β-Homophe-OH, 2-methyl-β-Phe-OH, 3-methyl-β-Phe-OH, 4-methyl-β-Phe-OH, β-Phe-OH, 4-(4-pyridyl)-β-Homoala-OH, 2-(trifluoromethyl)-β-Homophe-OH, 3-(trifluoromethyl)-β-Homophe-OH, 4-(trifluoromethyl)-β-Homophe-OH, 2-(trifluoromethyl)-β-Phe-OH, 3-(trifluoromethyl)-β-Phe-OH, 4-(trifluoromethyl)-β-Phe-OH, β-Tyr-OH, Ethyl 3-(benzylamino)propionate, β-Ala-OH, 3-(amino)-5-hexenoic acid, 3-(amino)-2-methylpropionic acid, 3-(amino)-2-methylpropionic acid, 3-(amino)-4-(2-naphthyl)butyric acid, 3,4-difluoro-β-Homophe-OH, γ,γ-diphenyl-β-Homoala-OH, 4-fluoro-β-Homophe-OH, β-Gln-OH, β-Homoala-OH, β-Homoarg-OH, β-Homogln-OH, β-Homoglu-OH, β-Homohyp-OH, β-Homoile-OH, β-Homoleu-OH, β-Homolys-OH, β-Homomet-OH, β-Homophe-OH, β3-homoproline, β-Homothr-OH, β-Homotrp-OH, β-Homotyr-OH, β-Leu-OH, 2-methyl-β-Homophe-OH, 3-methyl-β-Homophe-OH, β-Phe-OH, 4-3-pyridyl)-β-Homoala-OH, 3-(trifluoromethyl)-β-Homophe-OH, β-Glutamic acid, β-Homoalanine, β-Homoglutamic acid, β-Homoglutamine, β-Homohydroxyproline, β-Homoisoleucine, β-Homoleucine, β-Homomethionine, β-Homophenylalanine, β-Homoproline, β-Homoserine, β-Homothreonine, β-Homotryptophan, β-Homotyrosine, β-Leucine, β-Phenylalanine, Pyrrolidine-3-carboxylic acid and β-Dab-OH.

(PS) is a sulfated or non-sulfated polysaccharide chain including one or more monosaccharide units connected by glycosidic linkages. The polysaccharide chain (PS) may be any appropriate length. For instance, in some embodiments, the polysaccharide chain may include 1 to 100 monosaccharide unit(s), 1 to 90 monosaccharide unit(s), 1 to 80 monosaccharide unit(s), 1 to 70 monosaccharide unit(s), 1 to 60 monosaccharide unit(s), 1 to 50 monosaccharide unit(s), 1 to 40 monosaccharide unit(s), 1 to 30 monosaccharide unit(s), 1 to 20 monosaccharide unit(s), or even 1 to 10 monosaccharide unit(s). In some embodiments, the polysaccharide chain (PS) is a homopolysaccharide chain consisting of either pentose or hexose monosaccharide units. In other embodiments, the polysaccharide chain (PS) is a heteropolysaccharide chain consisting of one or both pentose and hexose monosaccharide units. In some embodiments, the monosaccharide units of the polysaccharide chain (PS) are selected from the group consisting of glucose, fructose, mannose, xylose and ribose. In some embodiments, the polysaccharide chain (PS) refers to a single monosaccharide unit (e.g., either glucose or fructose). In yet another aspect, the polysaccharide chain is an amino sugar where one or more of the hydroxy groups on the sugar has been replaced by an amine group. The connection to the carbonyl group can be either through the amine or a hydroxy group.

In some embodiments, for the pyrazine derivative of Formula I, at least one of either Y1 or Y2 is

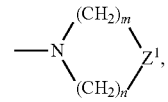

where $Z^1$ is a single bond, —$CR^1R^2$—, —O—, —$NR^1$—, —$NCOR^1$—, —S—, —SO—, or —$SO_2$—; and each of $R^1$ to $R^2$ are independently selected from the group consisting of H, —$CH_2(CHOH)_aH$, —$CH_2(CHOH)_aCH_3$, —$CH_2(CHOH)_aCO_2H$, —$(CHCO_2H)_aCO_2H$, —$(CH_2CH_2O)_cH$, —$(CH_2CH_2O)_cCH_3$, —$(CH_2)_aSO_3H$, —$(CH_2)_aNHSO_3H$, and —$(CH_2)_aPO_3H_2$; a, c, and m are as describe elsewhere herein.

In yet another aspect, at least one of $Y^1$ and $Y^2$ is —$NR^1R^2$, and $R^1$ to $R^2$ are as described above. In yet another aspect, both Y1 and Y2 are —NR1R2, and R1 to R2 are as described above. Alternatively, R1 and R2 are both independently selected from the group consisting of H, —CH2(CHOH)aCH3, —(CH2)aSO3H, —(CH2)aNHSO3H, and —(CH2)aPO3H2. In yet another aspect, both R1 and R2 are hydrogen.

Most preferably, the pyrazine is

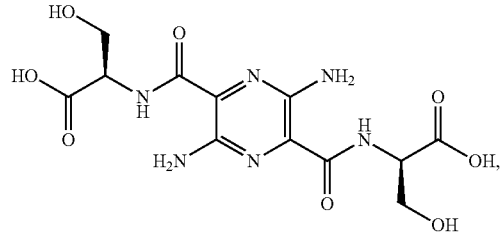 [SMILES: Nc1nc(C(=O)N[C@H](CO)C(=O)O)c(N)nc1C(=O)N[C@H](CO)C(=O)O]

or a pharmaceutically acceptable salt thereof.

In any aspect of the pyrazine compound, one or more atoms may alternatively be substituted with an isotopically labelled atom of the same element. For example, a hydrogen atom may be isotopically labelled with deuterium or tritium; a carbon atom may be isotopically labelled with 13C or 14C; a nitrogen atom may be isotopically labelled with 14N or 15N. An isotopic label may be a stable isotope or may be an unstable isotope (i.e., radioactive). The pyrazine molecule may contain one or more isotopic labels. The isotopic label may be partial or complete. For example, a pyrazine molecule may be labeled with 50% deuterium thereby giving the molecule a signature that can be readily monitored by mass spectrometry or other technique. As another example, the pyrazine molecule may be labeled with tritium thereby giving the molecule a radioactive signature that can be monitored both in vivo and ex vivo using techniques known in the art.

Pharmaceutically acceptable salts are known in the art. In any aspect herein, the pyrazine may be in the form of a pharmaceutically acceptable salt. By way of example and not limitation, pharmaceutically acceptable salts include those as described by Berge, et al. in J. Pharm. Sci., 66(1), 1 (1977), which is incorporated by reference in its entirety for its teachings thereof. The salt may be cationic or anionic. In some embodiments, the counter ion for the pharmaceutically acceptable salt is selected from the group consisting of acetate, benzenesulfonate, benzoate, besylate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate, diphosphate, polygalacturonate, salicylate, stearate, subacetate, succinate, sulfate, tannate, tartrate, teoclate, triethiodide, adipate, alginate, aminosalicylate, anhydromethylenecitrate, arecoline, aspartate, bisulfate, butylbromide, camphorate, digluconate, dihydrobromide, disuccinate, glycerophosphate, jemisulfate, judrofluoride, judroiodide, methylenebis(salicylate), napadisylate, oxalate, pectinate, persulfate, phenylethylbarbarbiturate, picrate, propionate, thiocyanate, tosylate, undecanoate, benzathine, chloroprocaine, choline, diethanolamine, ethylenediamine, meglumine, procaine, benethamine, clemizole, diethylamine, piperazine, tromethamine, aluminum, calcium, lithium, magnesium, potassium, sodium zinc, barium and bismuth. Any functional group in the pyrazine derivative capable of forming a salt may optionally form one using methods known in the art. By way of example and not limitation, amine hydrochloride salts may be formed by the addition of hydrochloric acid to the pyrazine. Phosphate salts may be formed by the addition of a phosphate buffer to the pyrazine. Any acid functionality present, such as a sulfonic acid, a carboxylic acid, or a phosphonic acid, may be deprotonated with a suitable base and a salt formed. Alternatively, an amine group may be protonated with an appropriate acid to form the amine salt. The salt form may be singly charged, doubly charged or even triply charged, and when more than one counter ion is present, each counter ion may be the same or different than each of the others.

All references herein to the "pyrazine", "pyrazine derivative", "pyrazine molecule", "pyrazine compound" or "pyrazine analog" apply to all compounds of Formula I. Additionally each reference to the pyrazine includes all pharmaceutically acceptable salts thereof unless specifically stated otherwise. Salt forms may be charged or uncharged, and may be protonated to form the appropriate cation or deprotonated to form the appropriate anion. All aspects and embodiments disclosed herein are applicable to compounds of Formula I, and specific examples are only illustrative and non-limiting to the scope of the disclosure.

In some aspects, the patient is suspected or known to have at least one medical impairment with their kidneys, and the methods disclosed herein are used to determine the level of renal impairment or deficiency present in the patient. In some aspects, the patient has an estimated GFR (eGFR) or previously determined GFR of less than 110, less than 90, less than 60, less than 30, or less than 15. The eGFR of a patient is determined using standard medical techniques, and such methods are known in the art. In some aspects, a patient will not have or not be suspected of having medical issues with their kidneys. The GFR monitoring may be done as part of a general or routine health assessment of a patient or as a precautionary assessment.

Because an increase of protein concentration in the urine of a patient may suggest some manner of kidney impairment or deficiency, the methods disclosed herein are suitable for patients whose urinalysis shows an increase in protein levels. In some aspects, the patient has an increased level of protein in their urine as determined by standard medical tests (e.g., a dipstick test). By way of example and not limitation, the urinalysis of a patient may show an increase in albumin, an increase in creatinine, an increase in blood urea nitrogen (i.e., the BUN test), or any combination thereof.

In some aspects, the patient has been previously diagnosed with at least Stage 1 CKD. In other aspects, the patient has been previously diagnosed with Stage 2 CKD, Stage 3 CKD, Stage 4 CKD or Stage 5 CKD. In yet another aspect, the patient has not yet been diagnosed with CKD but has one or more risk factors associated with CKD. In yet another aspect, the patient has no known risk factors for CKD.

Examples

Preparation of (2R,2'R)-2,2'-((3,6-diaminopyrazine-2,5-dicarbonyl)bis-(azanediyl))-bis(3-hydroxypropanoic acid) ("MB-102")

Samples of the MB-102 API were prepared and analyzed in accordance with GMP standards for use in the two clinical trials. The following procedure is representative.

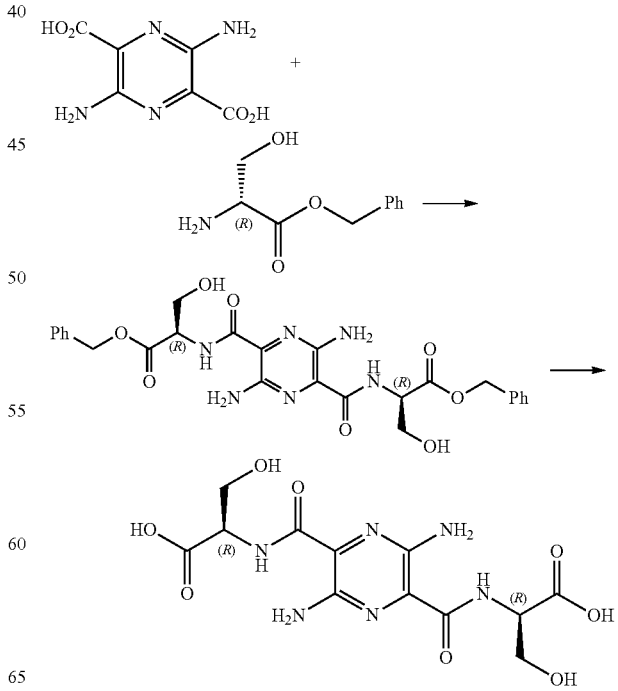

Step 1: Formation of dibenzyl 2,2'-((3,6-diaminopyrazine-2,5-dicarbonyl)-bis(azanediyl))(2R,2'R)-bis(3-hydroxypropanoate)

A 500 mL round-bottom flask equipped with a Claisen adapter and an addition funnel was charged with D-serine benzyl ester hydrochloride (24.33 g, 105.0 mmol) and anhydrous DMF (300 mL) was added by cannula. The solution was cooled in an ice-bath and stirred for 15 min under $N_2$ atmosphere. DIPEA (19.16 mL, 110.0 mmol) was added dropwise via addition funnel over a 30 min period, and after a further 30 min, the cooling bath was removed, and the diacid (9.91 g, 50.0 mmol) was added in one portion. The brick-red suspension was stirred for 30 min and HOBt·$H_2O$ (17.61 g, 115.0 mmol) was added in one portion. After 15 min, the reaction flask was cooled in an ice-bath, and EDC·HCl (22.05 g, 115.0 mmol) was added in portions over 15 minutes. The resulting suspension was slowly allowed to warm to room temperature and stirred overnight (ca. 17 h) under $N_2$.

The dark solution was concentrated to a syrupy residue under high vacuum (bath temp 60° C.) that was partitioned between EtOAc and milli-Q $H_2O$ (400 mL each). The layers were separated, and the aqueous layer was extracted with EtOAc (3×200 mL). The combined EtOAc extracts were successively washed with 0.50 M KHSO4, saturated NaHCO$_3$, H2O, and brine (250 mL each). Removal of the solvent under reduced pressure gave 23.7 g of an orange solid. The crude product was purified by flash chromatography over silica gel using a CHCl3:MeOH gradient to give the bis-amide (19.6 g, 71%) as an orange solid: Rf=0.45 [CHCl3:MeOH (9:1, v/v)]. 1H NMR (DMSO-d6) δ 8.56 (d, J=8.0 Hz, 2H, exchangeable with D20), 7.40-7.33 (m, 10H), 6.76 (s, 4H, exchangeable with D20), 5.37 (t, J=5.5 Hz, 2H), 5.20 (m, 4H), 4.66-4.63 (dt, J=8.0, 4.0 Hz, 2H), 3.97-3.93 (m, 2H), 3.81-3.77 (m, 2H). 13C NMR (DMSO-d6) δ 170.1, 164.9, 146.4, 135.8, 128.4, 128.0, 127.6, 125.9, 66.2, 61.1, 54.4; RP-LC/MS (ESI) m/z 553.3 (M+H)+(Rt=4.44 min, 5-95% B/6 min). Calc. for C26H28N6O8: C, 56.52; H, 5.11; N, 15.21. Found: C, 56.39; H, 5.11; N, 14.99.

Step 2: Formation of (2R,2'R)-2,2'-((3,6-diaminopyrazine-2,5-dicarbonyl)bis-(azanediyl))-bis(3-hydroxypropanoic acid)

The bisamide from Step 1 (7.74 g, 14.0 mmol) was hydrogenated in the presence of 10% Pd/C (0.774 g) in EtOH:$H_2O$ (560 mL; 3:1 v/v). The reaction mixture was purged with argon and stirred under hydrogen atmosphere (slow bubbling) at room temperature for 5.5 h. The reaction mixture was again purged with Ar, and the catalyst was removed by filtration over Celite. The bed was washed with EtOH:$H_2O$ (400 mL; 1:1 v/v), and the combined filtrates were concentrated in vacuo. The product was dried under high vacuum. The residue was triturated with $CH_3CN$ to give MB-102 (4.89 g, 94%) as an orange powder. $^1$H NMR (DMSO-d$^6$) δ 8.46 (d, J=8.3 Hz, 2H, exchangeable with D$_2$O), 6.78 (br s, 4H, exchangeable with D$_2$O), 4.48-4.45 (dt, J=8.1, 3.9 Hz, 2H), 3.88 (dd, J=11.1, 3.9 Hz, 2H), 3.74 (dd, J=11.1, 3.7 Hz, 2H). $^{13}$C NMR (DMSO-d$^6$) δ 171.6, 164.7, 146.4, 125.9, 61.2, 54.3. RPLC/MS (ESI) m/z 373.2 (M+H)+(R$_t$=2.86 min, 5-95% B/6 min). Anal. Calc. for $C_{12}H_{16}N_6O_8$: C, 38.71; H, 4.33; N, 22.57. Found: C, 38.44; H, 4.51: N, 22.33.

Sample Preparation for Direct Dilution Analysis

For sample preparation by direct dilution, calibration standards containing 0.4, 1.0, 2.0, 4.0, 10.0, 16.0, 40.0, 100.0, 200.0, 400.0 ng/mL and quality controls at low, mid, and high level of MB-102 were prepared in 1% human plasma in PBS on the day of the validation study or sample analysis. The MB-102 dosing solution (18.6 mg/mL) used in the clinical study was diluted 1/100 first with 1% human plasma in PBS to form a stock solution of 186 µg/mL MB-102. This stock solution is diluted further with 1% human plasma in PBS to form a calibration standard working stock of 2000 ng/mL MB-102 for preparation of calibration standards. A QC working stock at (300 ng/mL) was also prepared from the 186 µg/mL MB-102 stock by dilution with 1% plasma in PBS. The low, mid, and high levels of quality controls were prepared from this QC working stock by dilution with 1% human plasma in PBS.

Sample Preparation for Protein Precipitation Analysis

For sample preparation by protein precipitation, calibration standards containing 0.4, 1.0, 2.0, 4.0, 10.0, 16.0, 40.0, 100.0, 200.0, 400.0 ng/mL and quality controls at low, mid, and high level of MB-102 were prepared as follows. Ten thousand fold concentration of MB-102 in 1×PBS were prepared for each standards and QCs. These stock solutions were diluted 1/100 with plasma to make the working calibration standards and QCs of MB-102 in 99% plasma/1% PBS. 200 µL of these working standards and QCs were aliquoted into 600 µL vials and stored at −80° C. until use. Using the same HPLC method, these working calibration standards and QCs were qualified and certified for analysis of unknown samples.

Analysis of Patient Samples

Plasma samples were obtained from the two clinical studies. All plasma samples were stored at −80° C. until analysis.

For the samples being analyzed by direct dilution, 10 µL of plasma sample (thawed to room temperature and mixed thoroughly) was diluted with 990 µL 1×PBS, mixed thoroughly for about 10 minutes, and centrifuged at 1000 rpm for 2 minutes. It was directly analyzed by HPLC.

For the samples being analyzed by protein precipitation, 50 µL of plasma (thawed to room temperature and mixed thoroughly) was diluted with 200 µL of methanol containing 4.5% of 1×PBS (v/v), mixed for at least 10 seconds, and centrifuged for at >4000 rpm for 10 minutes. The entire supernatant was transferred to a second container. From there, 50 L of supernatant was mixed with 950 µL of 1×PBS. The sample was mixed and analyzed by HPLC. With this procedure, the dry-down of supernatant after plasma protein precipitation is eliminated. A portion of the supernatant was diluted directly with 1×PBS for HPLC analysis so that the internal standard commonly used in the protein precipitation method is not needed.

HPLC Analysis

Analyses were performed on a Waters Acquity UPLC H Class Chromatography System, equipped with column heater, sample heater/cooler, vacuum degasser, autosampler, fluorescence detector, and pump capable of delivering a binary gradient. An HPLC analytical column, Phenomenex Luna C18 (2), 4.6×250 mm, 5 µm, 100 Å (Phenomenex, Cat. No. 00G-4252-E0, S/N H15-133556), and a Security Guard Cartridge C18, 4×3 mm ID, 5 µm (Phenomenex, Cat. No. KJ0-4282) were used for the analysis. The Waters Empower 3 software equipped with the UPLC system was used for assay setup, analysis monitoring, and data processing. Two mobile phases, Mobile Phase A: 0.1% Trifluoroacetic acid in water (Fisher, Optima® Grade) and Mobile Phase B: 0.1% Trifluoroacetic acid in acetonitrile (Fisher Scientific, Optima® Grade) were used. The column temperature was set at 30° C., the autosampler temperature was set at 5° C., the excitation wavelength was set at 434 nm and the detection/emission wavelength was set at 556 nm. The counting rate was set at 5 point/sec; the PMT gain was set at 50; the flow cell temperature was ambient; the injection volume was 10 μL. MB-102 elutes at about 3.6 minutes using the gradient shown.

| Time (min.) | Flow Rate (mL/min) | % A | % B | Gradient Curve |
|---|---|---|---|---|
| 0.00 | 1.1 | 85 | 15 | 6 |
| 5.00 | 1.1 | 40 | 60 | 6 |
| 5.05 | 1.6 | 10 | 90 | 6 |
| 6.75 | 1.6 | 10 | 90 | 6 |
| 6.80 | 1.1 | 85 | 15 | 6 |
| 10.00 | 1.1 | 85 | 15 | 6 |

Method Validation

Using this HPLC method and sample preparation described herein, a validation study was carried out to determine the precision, accuracy, linearity, reproducibility, plasma and sample solution stability, freeze-thaw stability, lowest limits of quantitation, and specificity. The acceptance criterion was ±15% data deviation from normal values excepted at the lowest limit of quantitation (LLOQ) where it was set at ±20%. Samples were analyzed both in-house and at a GMP contract lab to ensure both the validity of the method and accuracy of the results.

Specificity and Selectivity

The interference of plasma components with MB-102 and the analysis was investigated by comparing chromatograms of blank samples to those spiked with MB-102. The LLQ was determined to be at least 10 times the noise level on blank samples while the LLOD was determined to be at least three times the noise level on blank samples.

Accuracy and Precision

Three replicates of samples preparations at five concentration levels of MB-102 in 1% plasma/PBS were made and analyzed for accuracy determination. For precision determination of instrument injection, ten injections of a 200 ng/mL sample were done to ensure that repeated injections are highly precise.

Recovery

The recovery was determined at three different concentrations of MB-102 by comparing plasma sample controls to those plasma samples spiked with MB-102. The percentage of MB-102 recovered from the spiked samples was determined as % of recovery.

Plasma Sample Stability and Plasma Solution Stability

MB-102 stability during sample handling upon long term storage of plasma samples (frozen at −80° C.) and short-term storage (bench top ambient temperature with/without light exposure, and 2-8° C.) of plasma solution was evaluated. Plasma samples were tested for three freeze/thaw cycles (−80° C. to room temperature). The stability of MB-102 in plasma solution at room temperature with/without light exposure, at 2-8° C., and at auto-sampler temperature (5° C.) was evaluated for time intervals of 24 and 48 hours.

Results

Figure 2:
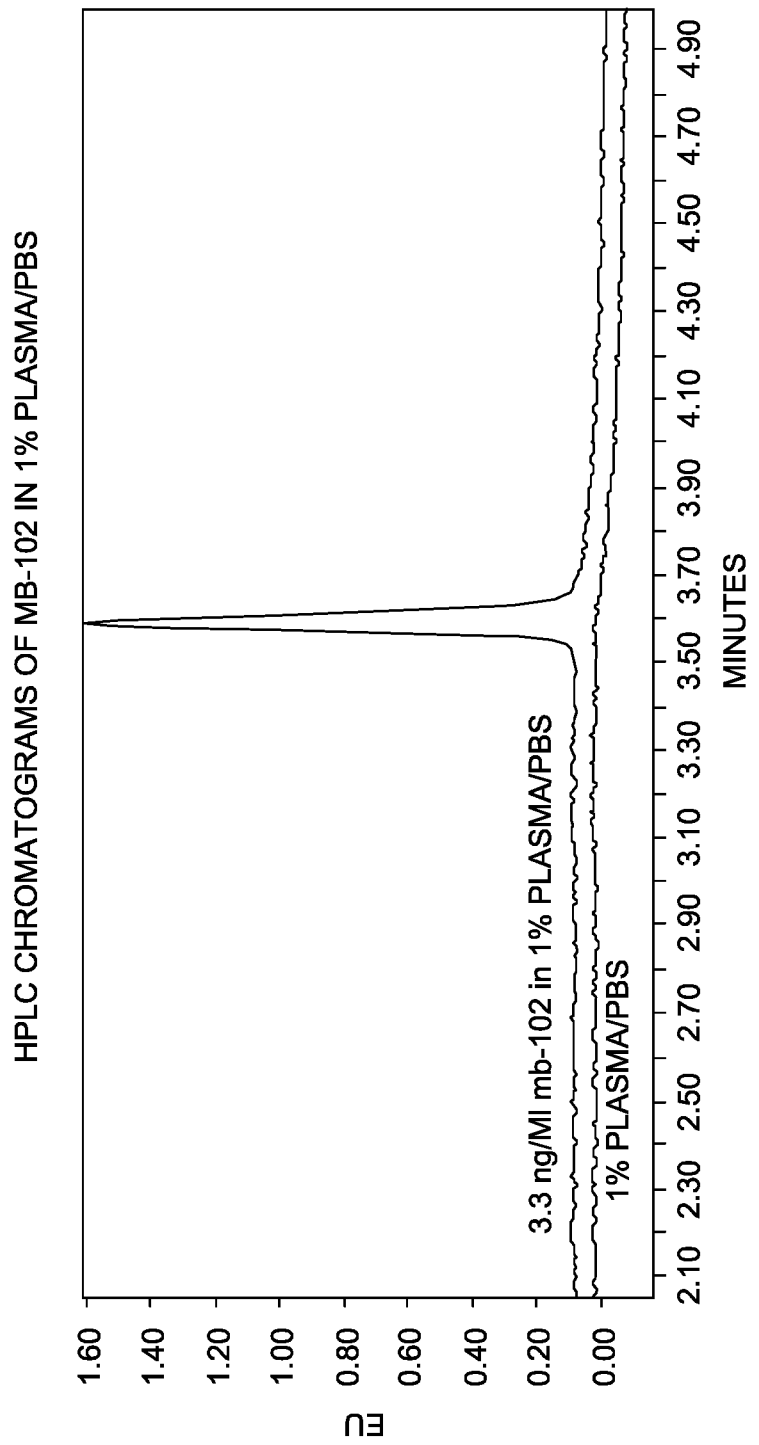
FIG. 2 is an overlay of the HPLC chromatograms of MB-102 at 3.3 ng/mL in 1% plasma/PBS with a control blank (1% plasma/PBS).

FIG. 2 illustrates an overlay of the HPLC chromatograms of MB-102 (3.3 ng/mL in 1% plasma/PBS) with a blank control (1% plasma/PBS). The fluorescence wavelength emitted from MB-102 at 556 nm was monitored for quantitation. The 1% of plasma proteins in the sample solution do not have a peak eluted near 3.62 min to interfere with MB-102 for detection or quantitation.

Method Validation

Figure 3A:
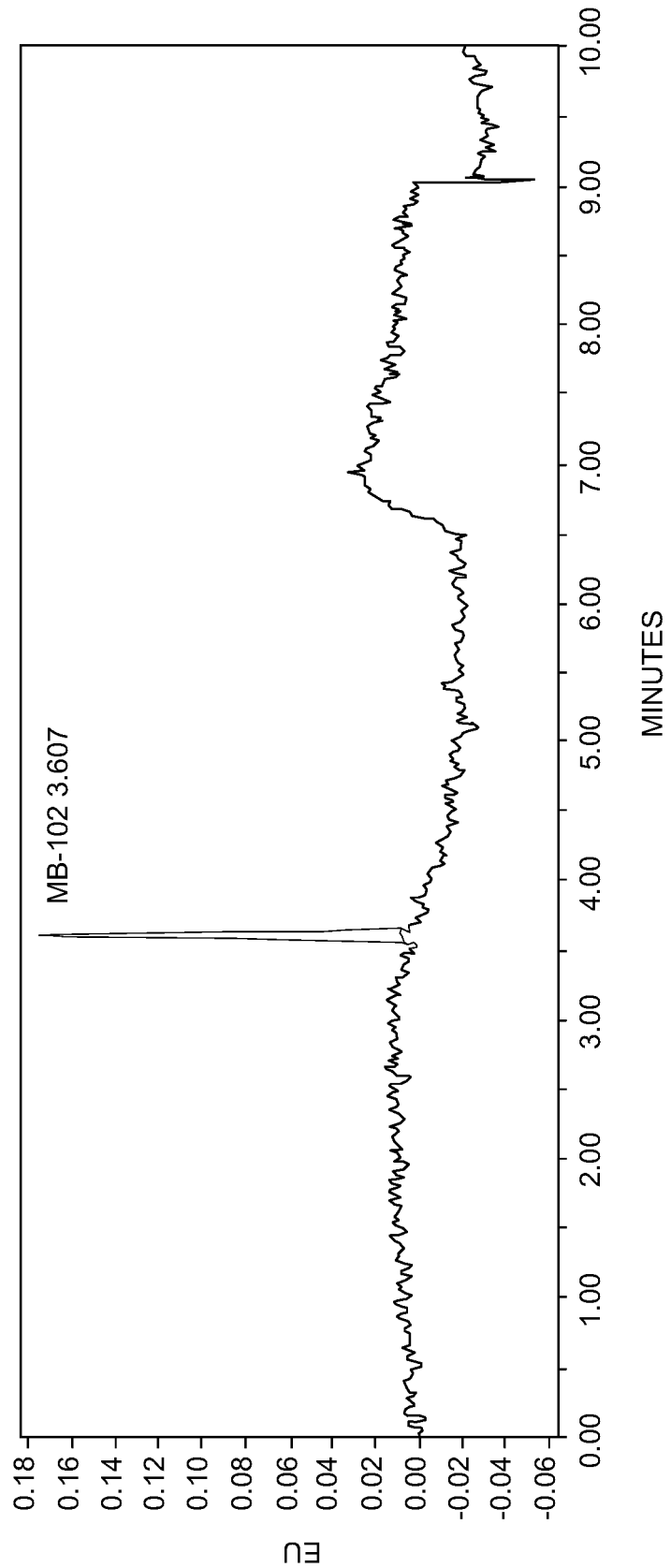
FIGS. 3A and 3B illustrate the signal/noise, USP Tailing Factor, and USP plate count of MB-102 at 0.4 ng/mL in 1% plasma/PBS for two different samples.
Figure 3B:
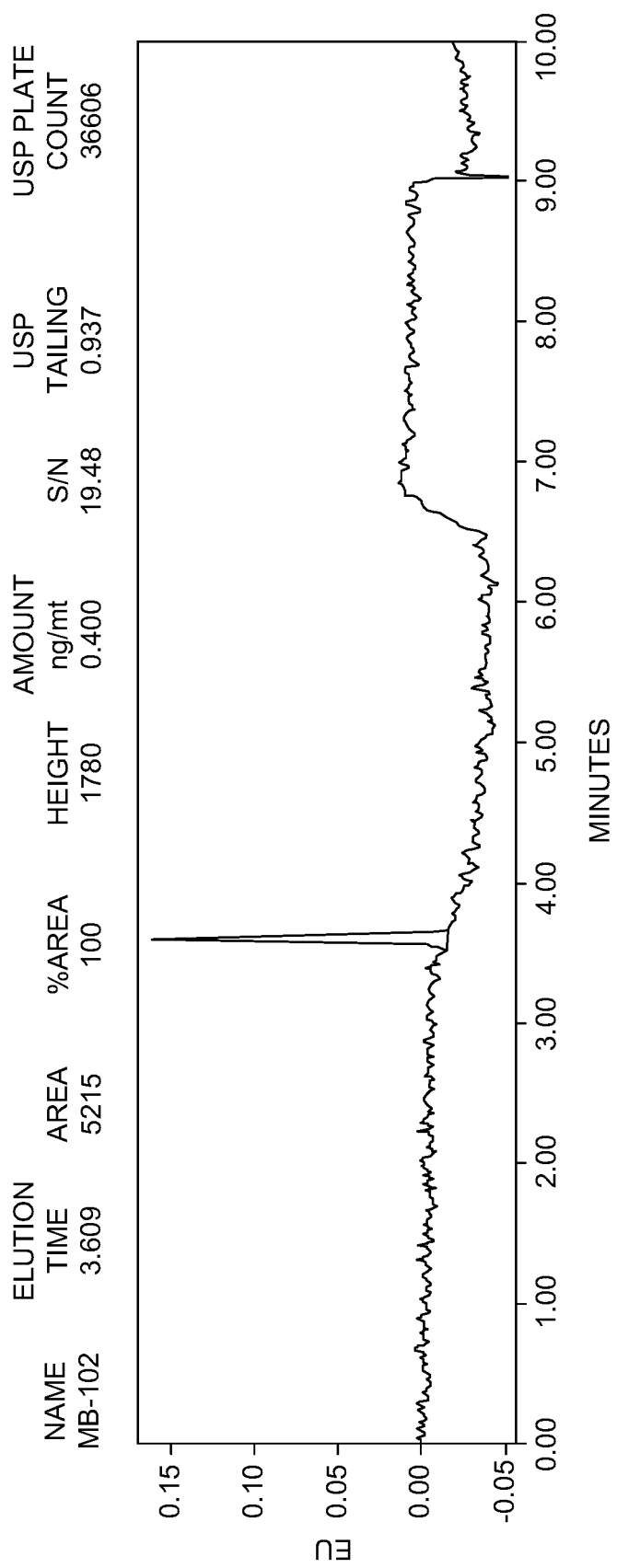

The results of the method validation study are summarized in Table 1. MB-102 standards calibration showed a very good linear response over three orders of magnitude for concentrations of from 0.4 ng/mL to 400 ng/mL with an $R^2$ of 0.9997 using a linear regression with a weighing of 1/x. The LLOQs at 0.4 ng/mL has a signal/noise ratio of 15.18, USP Tailing of 1.072, and USP plate count of 39934 as shown in FIG. 3A. An improved signal/noise ratio (19.48) was obtained with additional refining of the instrument (FIG. 3B).

TABLE 1

Results of Method Validation Studies

| Concentration of MB-102 (ng/mL) | Number of Observations | Mean Concentration (ng/mL) | RSD (%) | % Recovered |
|---|---|---|---|---|
| 380.0 | 3 | 384.7 | 0.73 | 101.2 |
| 160.0 | 3 | 159.6 | 0.80 | 99.7 |
| 60.0 | 3 | 59.3 | 0.76 | 98.8 |
| 20.0 | 3 | 19.8 | 1.46 | 99.2 |
| 3.0 | 3 | 2.9 | 3.20 | 95.7 |
| Injection Precision | | | | |
| 200.0 | 10 | 198.5 | 0.45 | 99.2 |
| Linearity | | | | |
| 0.4 | 3 | 0.4 | 4.30 | 105.0 |
| 1.0 | 3 | 1.0 | 3.39 | 101.0 |
| 2.0 | 3 | 2.0 | 1.44 | 100.0 |
| 4.0 | 3 | 4.0 | 3.40 | 100.3 |
| 10.0 | 3 | 9.9 | 2.08 | 98.7 |
| 16.0 | 3 | 15.4 | 2.33 | 96.4 |
| 40.0 | 3 | 39.8 | 1.20 | 99.6 |
| 100.0 | 3 | 99.2 | 1.35 | 99.2 |
| 200.0 | 3 | 199.2 | 0.45 | 99.6 |
| 400.0 | 3 | 402.4 | 0.49 | 100.6 |
| Slope | 3 | 1.30E+04 | 1.61 | |
| $R^2$ | 3 | 0.9999 | 0.01 | |
| 3 Freeze/Thaw cycles | | | | |
| 1.76 | 3 | 1.79 | 1.09 | 101.7 |
| 8.81 | 3 | 8.81 | 1.79 | 100.0 |
| 61.87 | 3 | 62.34 | 1.82 | 100.8 |
| Sample Solution Stability at 4° C. for 48 hours | | | | |
| 1.76 | 3 | 1.75 | 2.56 | 99.4 |
| 8.81 | 3 | 8.66 | 2.06 | 98.3 |
| 61.87 | 3 | 60.84 | 3.47 | 98.3 |
| QCs Prepared at three days stored at 4° C. for 48 hours | | | | |
| 3.7 | 1 | 3.74 | N/A | 101.1 |
| 37.9 | 1 | 37.55 | N/A | 99.1 |
| 372.6 | 1 | 373.50 | N/A | 100.2 |
| QCs Prepared at three days stored at RT without light | | | | |
| 3.7 | 1 | 3.87 | N/A | 104.6 |
| 37.9 | 1 | 37.15 | N/A | 98.0 |
| 372.6 | 1 | 372.58 | N/A | 100.0 |
| QCs Prepared at three days stored at RT with light | | | | |
| 3.7 | 1 | 3.76 | N/A | 101.6 |
| 37.9 | 1 | 36.40 | N/A | 96.0 |
| 372.6 | 1 | 364.59 | N/A | 97.9 |
| Recovery of MB-102 spiked into Plasma | | | | |
| 0.6 | 3 | 0.67 | 4.24 | 111.7 |
| 6.0 | 3 | 6.14 | 5.48 | 102.3 |
| 60.0 | 3 | 60.25 | 2.9 | 100.4 |

Figure 4:
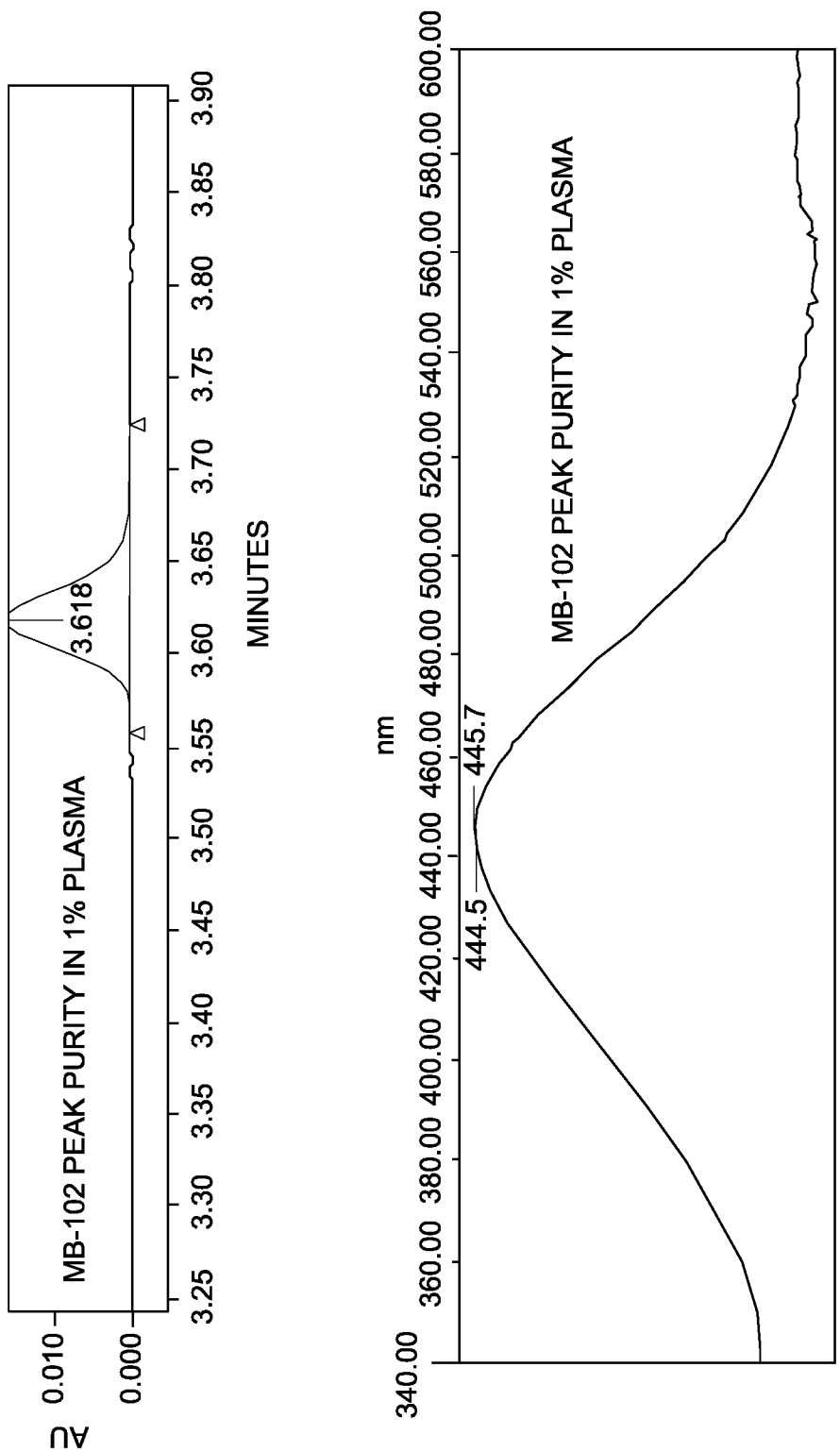
FIG. 4 is the peak purity of MB-102 spiked into 1×PBS.
Figure 5:
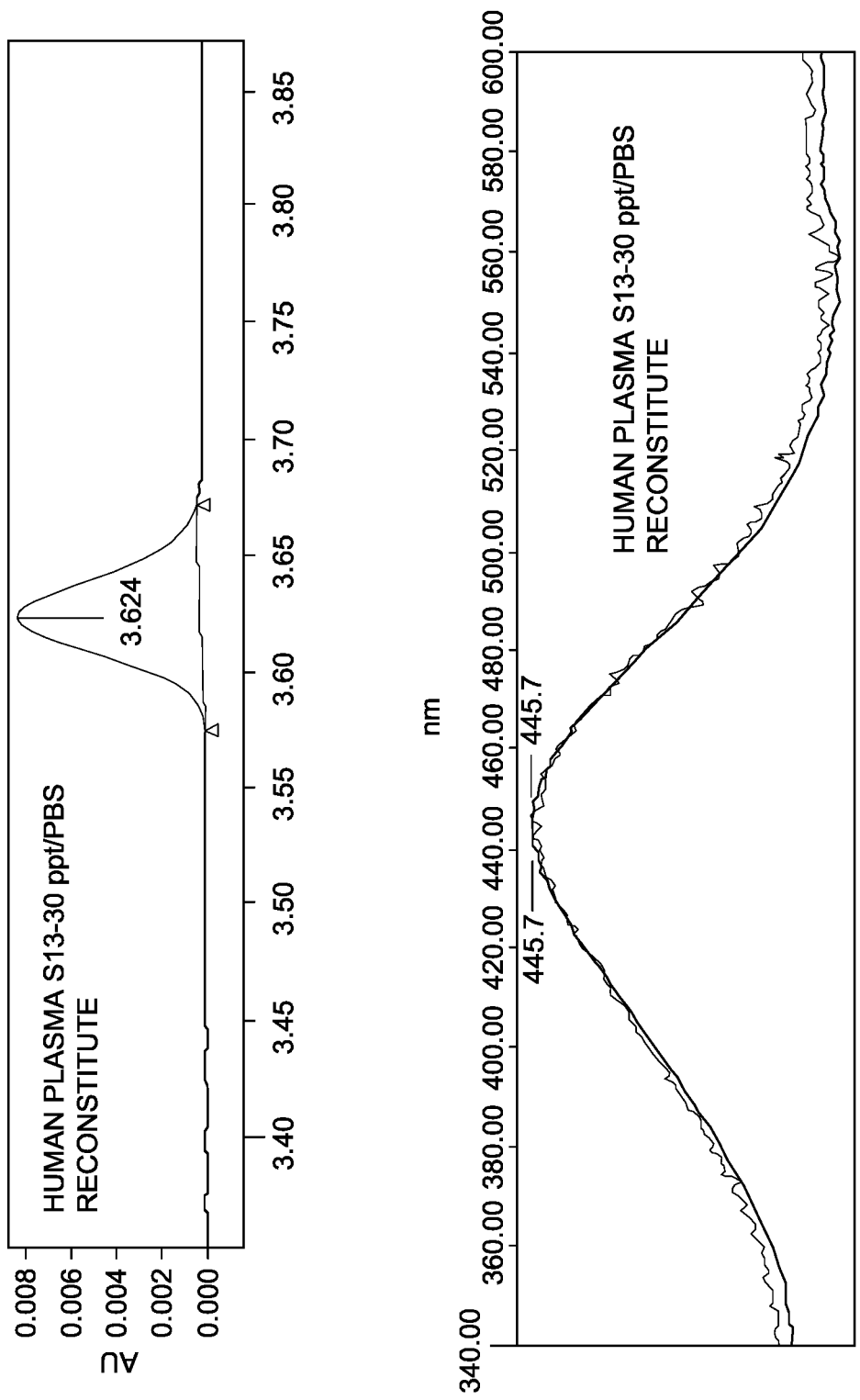
FIG. 5 is the peak purity of MB-102 in a plasma sample after standard sample preparation.

The assay precision was excellent showing a 99.2% recovery, a 0.45% RSD, and accuracy ranging from 95.7% to 101.2% recovery for all conditions studied. Three freeze/thaw cycles indicate that the plasma is very stable at −80° C. The sample solution stability stored at 4° C. and at room temperature without light for up to 48 hours is also very stable. There is a small degradation (~1-2%) of MB-102 when the solution was stored at room temperature with light for 48 hours. All three concentrations of spike recovery were within ±15% of the amount spiked. To determine the purity of MB-102 peak eluted at 3.62 minutes for the unknown sample, the plasma sample was protein precipitated, the supernatant was dried down and reconstituted into PBS. The HPLC chromatograms monitored at 445 nm (in PDA mode) were generated. The MB-102 PDA peak purity from a spiked sample in PBS was compared with that of a plasma sample collected from the clinical study. The results as shown in FIG. 4 and FIG. 5 indicated that the MB-102 peak eluted at 3.62 minutes that absorbs at 445 nm from the clinical study is pure.

Analysis of Samples from Patients

In support of the clinical studies to evaluate the utility of MB-102 for kidney function monitoring via transdermal fluorescence sensing, the plasma samples were prepared from blood samples collected at 0, 5, 10, 15, 30, 60, 90, 120, 180, 240, 300, 360, 480, 600, and 720 minutes of each study participant. This method was transferred to a GMP certified bioanalytical lab for validation and analysis of plasma samples of the entire clinical study. The results from the GMP laboratory were compared to the results from in-house testing to ensure both accuracy and reproducibility.

Figure 6:
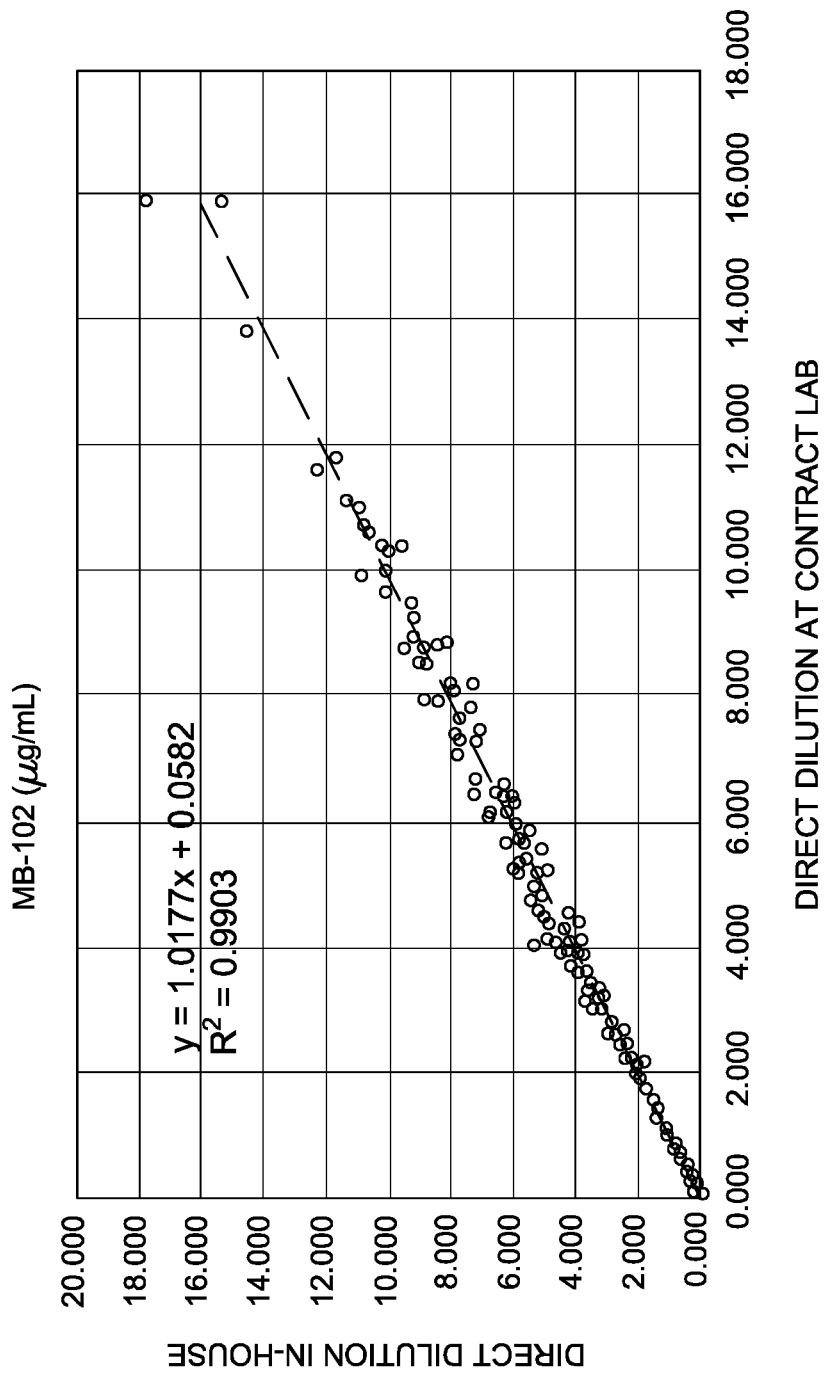
FIG. 6 is a graph of the correlation of MB-102 in plasma obtained from patients as tested at the GMP contract lab versus in-house evaluation.
Figure 7:
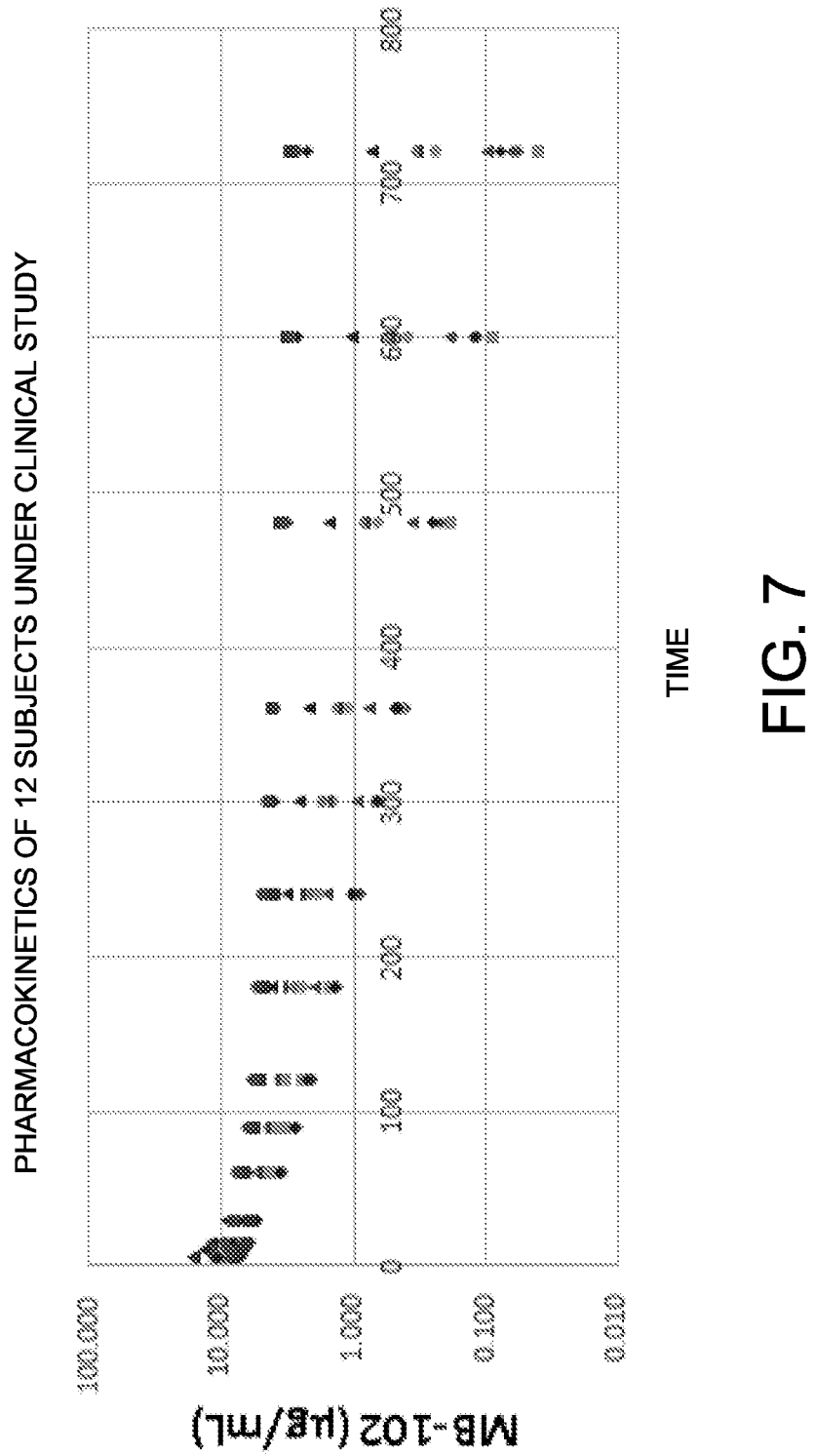
FIG. 7 is the pharmacokinetic analysis of MB-102 on 12 patients from the clinical trials.

Plasma samples from 12 patients from the same study were used in-house to validate the GMP laboratory results. A comparison of the results from these subjects obtained in-house and the GMP lab is shown in FIG. 6. A linear regression of the correlation indicates a slope of 1.018 with an $R^2$ of 0.9903. The pharmacokinetic analysis from these 12 subjects is shown in FIG. 7 and indicates that the clearance rate of MB-102 varies among patients.

Figure 8B:
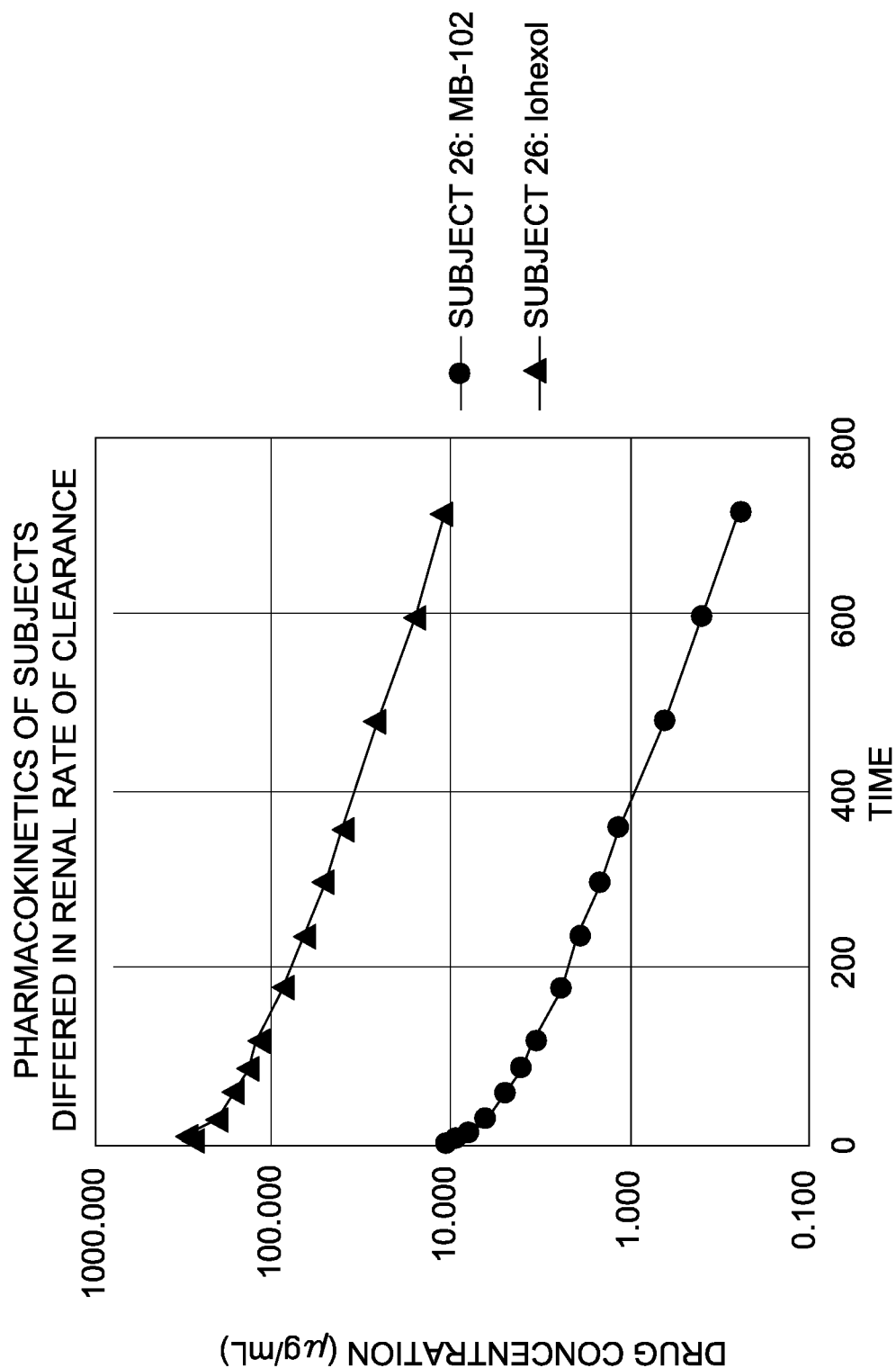
Figure 8C:
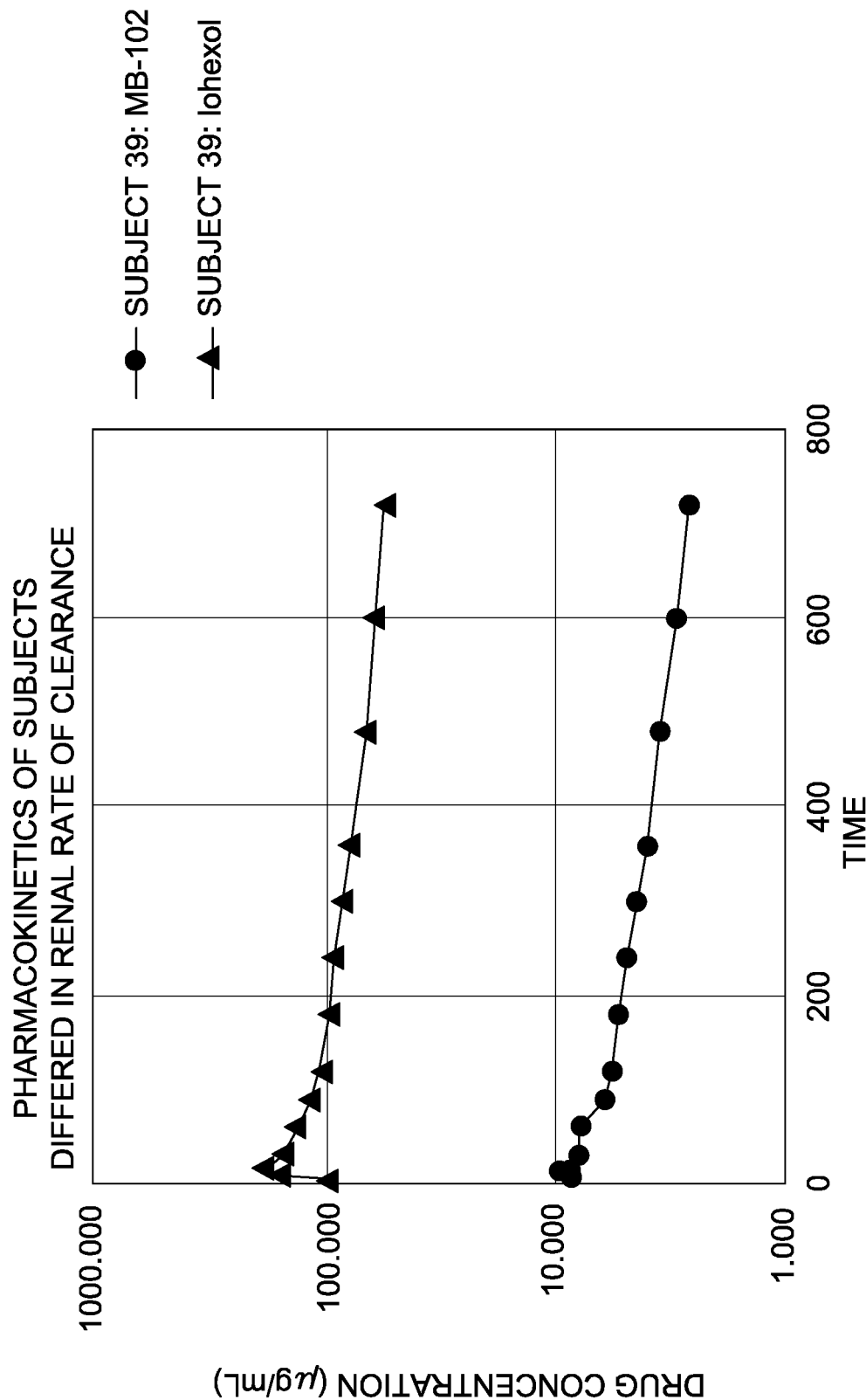

Since iohexol was co-dosed with MB-102 in this study as a reference marker, a comparison of the pharmacokinetics of MB-102 and iohexol on three subjects is illustrated in FIGS. 8a, 8b and 8c. As shown in the figures, the clearance rate of MB-102 is parallel to that of iohexol for each of the three subjects illustrated here. Therefore MB-102 can perform similarly to iohexol for GFR determination.

Figure 9:
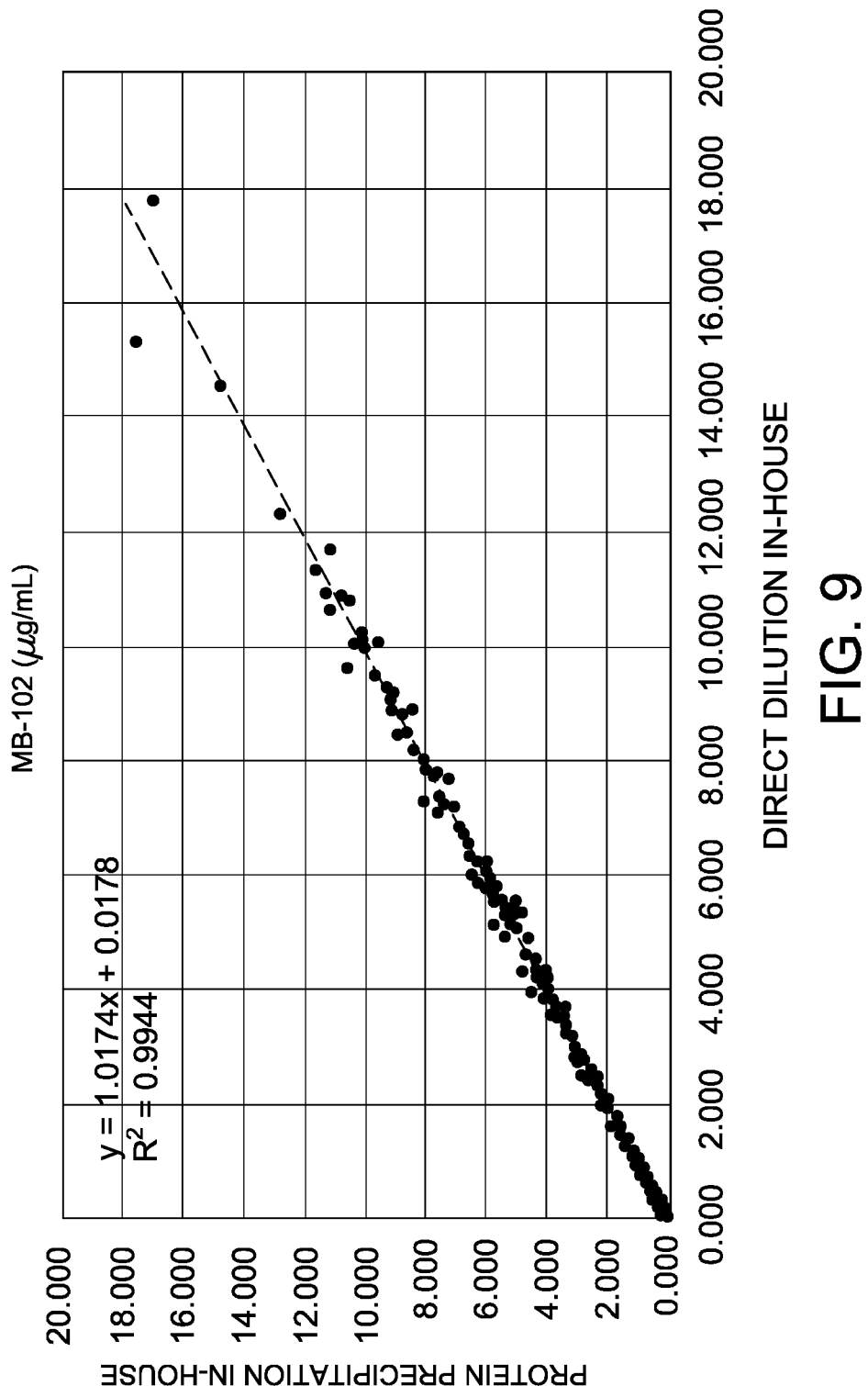
FIG. 9 is a graph of the correlation of MB-102 in plasma as tested using either direct dilution or protein precipitation.

To better understand the correlation of 1.0177 as shown in FIG. 6 when comparing the measurements made in-house versus the GMP contract lab, the traditional method of plasma sample preparation by protein precipitation for HPLC analysis was investigated. The plasma samples from the same 12 subjects were analyzed using a modified protein precipitation method. The correlation plot of MB-102 determined by direction dilution method vs. protein precipitation method is shown in FIG. 9. The results with a correlation slope of 1.0074 and $R^2$ of 0.9944 strongly support the validity of analyzing MB-102 content in plasma prepared by the direct dilution method. Preparation of plasma samples by protein precipitation is time consuming and requires set up of additional laboratory equipment. Preparing plasma samples by 1/100 direct dilution in 1×PBS is easy, fast, precise and accurate.

Figure 10:
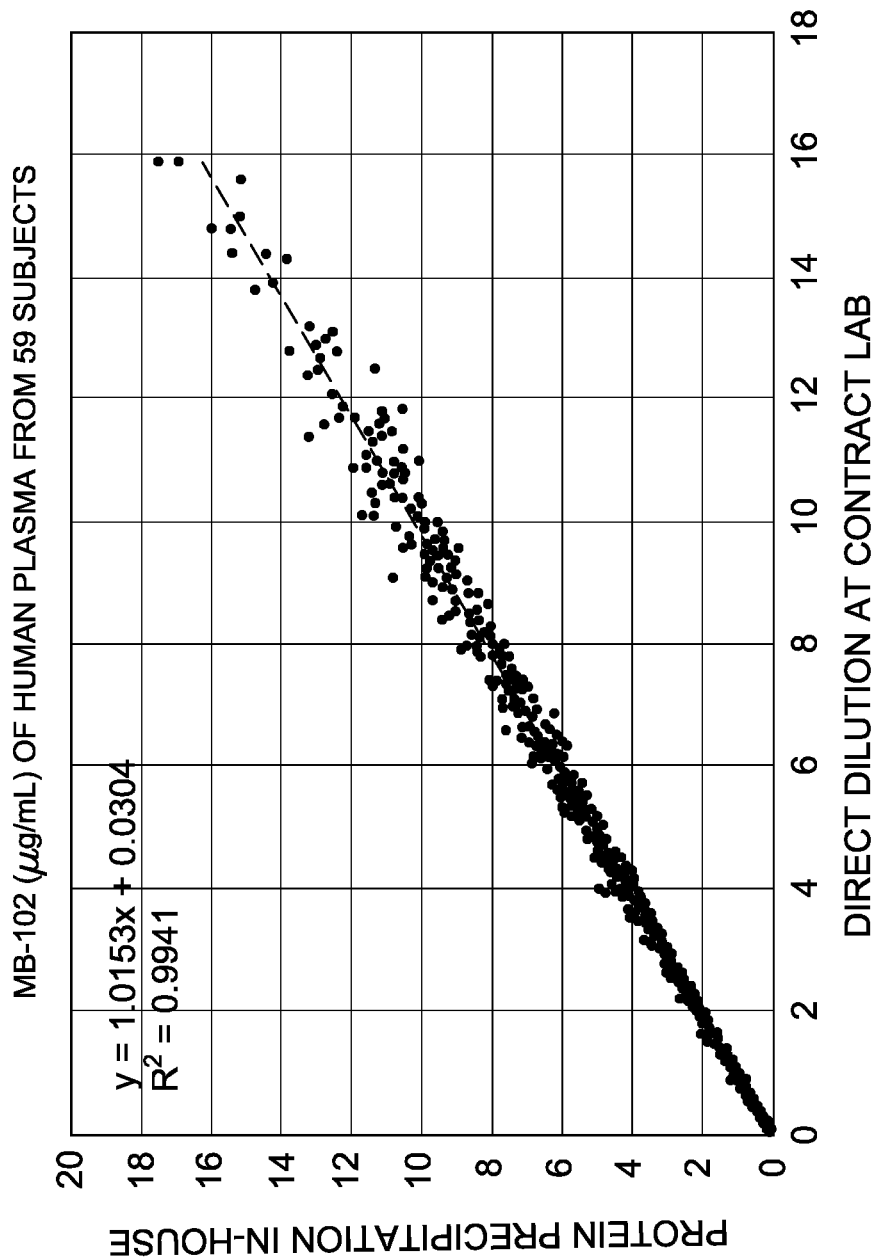
FIG. 10 is a graph of the correlation of MB-102 concentration in plasma tested by direct dilution for samples tested in-house versus the GMP contract lab.

Using the protein precipitation method, the plasma samples from the clinical study of 59 subjects were analyzed. The results were compared with those obtained from the GMP laboratory using the direct dilution method. The correlation plot of these two set of data is illustrated in FIG. 10. A correlation slope of 1.0153 with an $R^2$ of 0.9941 was obtained. The p-value (0.579>0.05) from this data using a two sample t-test assuming equal variances indicates that the means of the pairs are not statistically different.

Analysis of Blood Samples Showing Hemolysis

Figure 11:
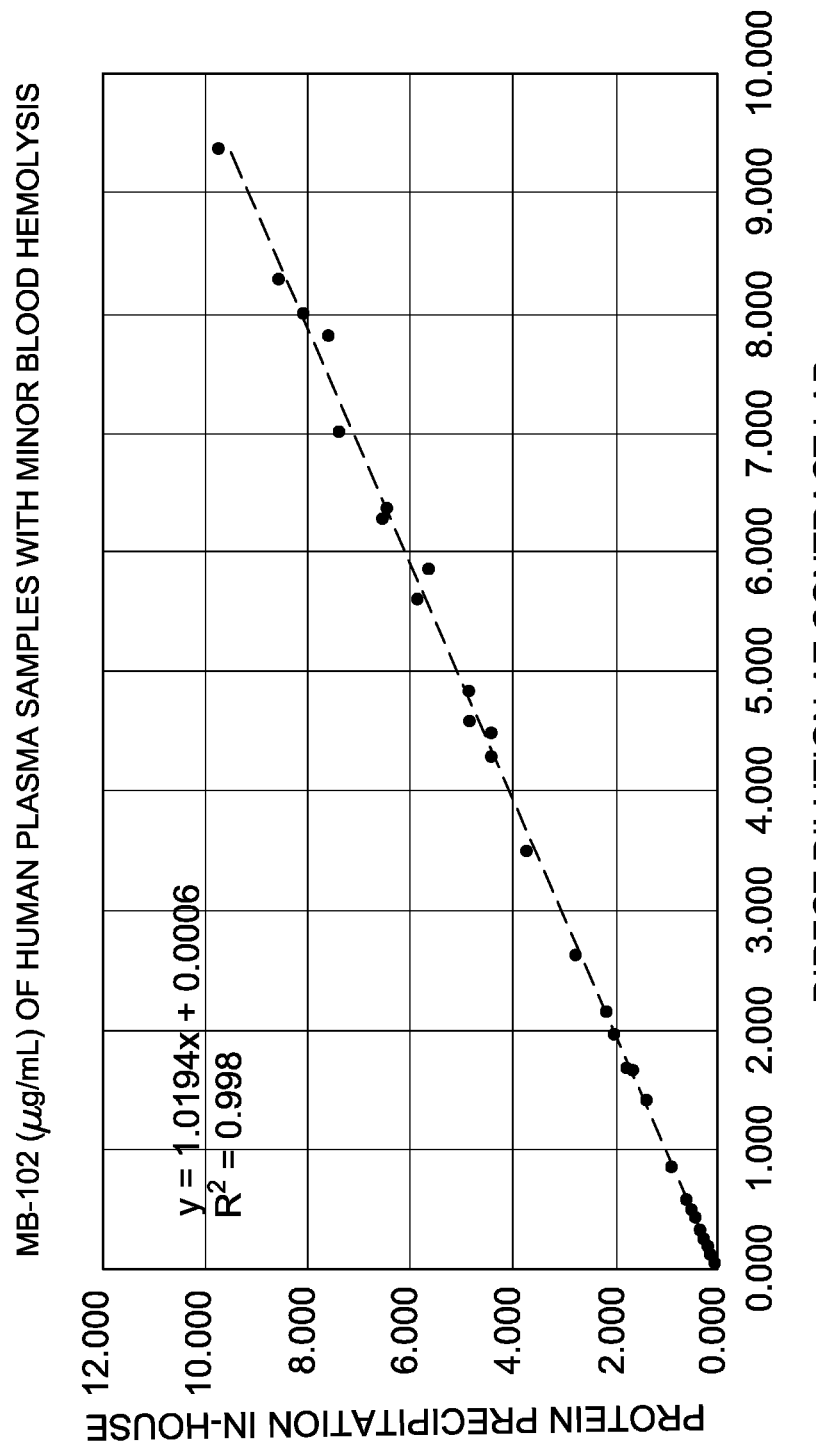
FIG. 11 is a graph of the correlation of the MB-102 concentration in plasma samples showing hemolysis (hemoglobin levels between 50 mg/dL and 100 mg/dL) as tested by direct dilution and protein precipitation.

During the development of the methods disclosed herein, the effects of hemolysis on MB-102 quantitation in plasma was investigated. Clinical protocol to minimize hemolysis during blood collection and plasma preparation was conveyed and discussed with the clinicians at the trial site; however, among all of the plasma samples of 59 subjects, several samples with some degree of hemolysis were noted. Greater than 90% of plasma samples received from the clinical study had a hemoglobin content 50 mg/dL and under. Several of the plasma samples had a hemoglobin content around 100 to 250 mg/dL. The MB-102 concentration of these samples was compared using the direct dilution and protein precipitation methods. The results in FIG. 11 are for samples having a hemoglobin content between 50 mg/dL and 100 mg/dL. The slope (1.0194) of the correlation curve indicated that the impact MB-102 quantitation is minimal when compared it with the slope (1.0153) of correlation curve shown in FIG. 10.

Figure 12:
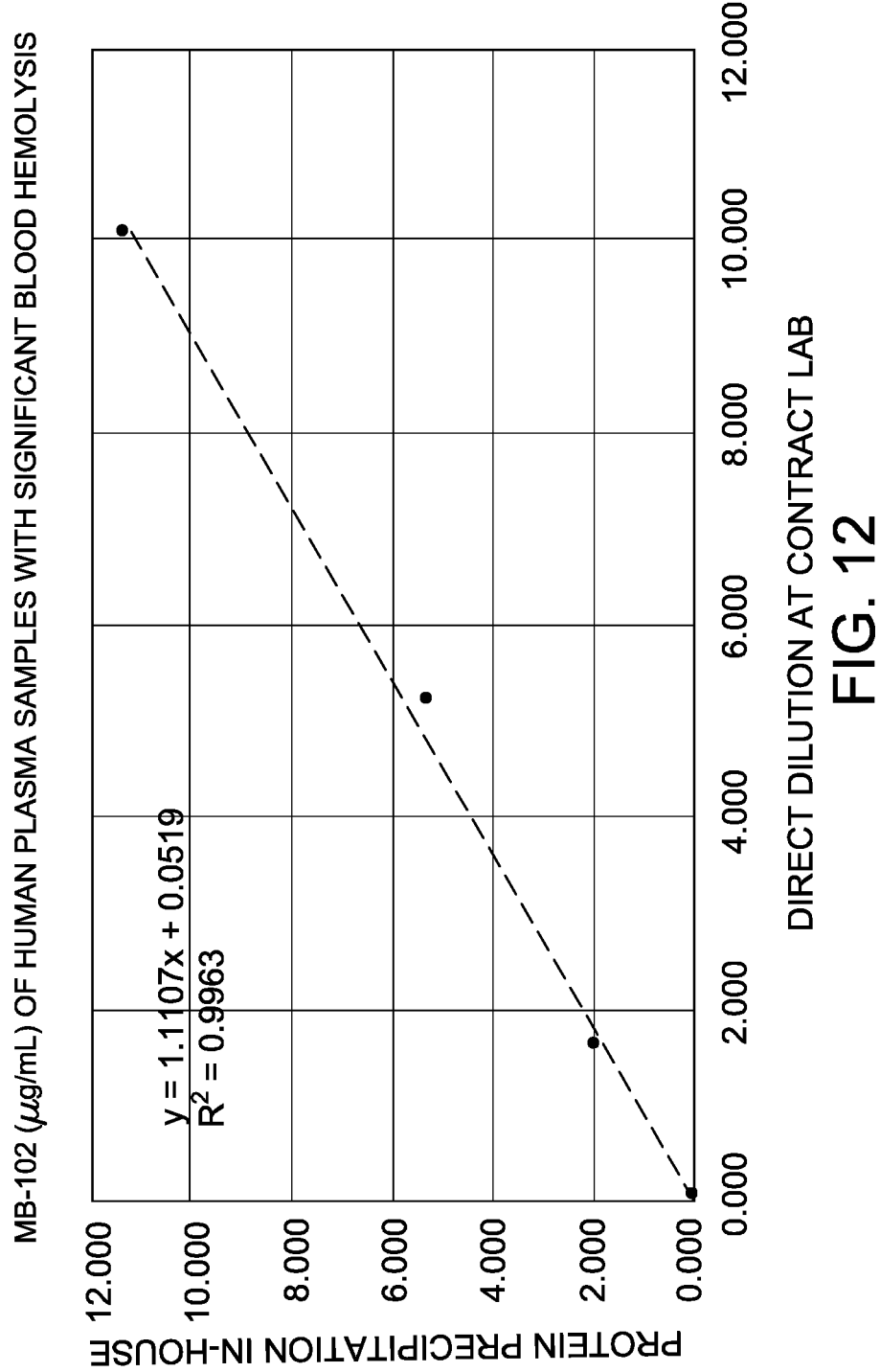
FIG. 12 is a graph of the correlation of the MB-120 concentration in plasma samples showing hemolysis (hemoglobin levels between 100 mg/dL and 250 mg/dL) as tested by direct dilution and precipitation.

The results in FIG. 12 are the samples exhibiting a hemoglobin content between 100 mg/dL and 250 mg/dL. The slope (1.1107) of the correlation curve indicates an impact on MB-102 quantitation when compared with the slope (1.0153) of the correlation curve shown in FIG. 10. Since these four plasma samples were from four different subjects at different time point of sample collection, their impact on determining the clearance rate, and thus the GFR, will not be significant.

The data from these studies indicates that both the direct dilution and precipitation methods with fluorescence detection are precise and accurate and suitable for assaying MB-102 in human plasma.

What is claimed is:

1. A method for measuring the amount of a fluorescent compound in plasma, the method comprising:

diluting a sample of plasma comprising the fluorescent compound with an aqueous buffer; and analyzing the diluted sample by high performance liquid chromatography (HPLC) thereby measuring the amount of the fluorescent compound in the sample of plasma;

wherein the sample of plasma is not dried before HPLC analysis, and no internal standard is added to the sample, wherein the method does not include a protein precipitation step that comprises causing proteins to precipitate from the sample of plasma and removing the precipitated proteins from the sample prior to HPLC analysis, wherein the fluorescent compound is a compound of Formula I, or a pharmaceutically acceptable salt thereof, wherein

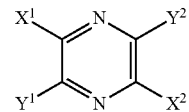

Formula I each of $X^1$ and $X^2$ is independently $—CO_2R^1$, $—CONR^1R^2$, $—CO(AA)$ or $—CONH(PS)$;

each of $Y^1$ and $Y^2$ is independently selected from the group consisting of $—NR^1R^2$; and $$-\text{N} \begin{array}{c} (CH_2)_m \\ \diagdown \\ \diagup \\ (CH_2)_n \end{array} Z^1;$$

$Z^1$ is a single bond, —$CR^1R^2$—, —O—, —$NR^1$—, —$NCOR^1$—, —S—, —SO—, or —$SO_2$—;

each of $R^1$ to $R^2$ are independently selected from the group consisting of H, —$CH_2(CHOH)_aH$, —$CH_2(CHOH)_aCH_3$, —$CH_2(CHOH)_aCO_2H$, —$(CHCO_2H)_aCO_2H$, —$(CH_2CH_2O)_cH$, —$(CH_2CH_2O)_cCH_3$, —$(CH_2)_aSO_3H$, —$(CH_2)_aSO_3^-$, —$(CH_2)_aSO_2H$, —$(CH_2)_aSO_2^-$, —$(CH_2)_aNHSO_3H$, —$(CH_2)_aNHSO_3^-$, —$(CH_2)_aNHSO_2H$, —$(CH_2)_aNHSO_2^-$, —$(CH_2)_aPO_3H_2$, —$(CH_2)_aPO_3H^-$, and —$(CH_2)_aPO_3^{2-}$;

AA is a peptide chain comprising one or more amino acids selected from the group consisting of natural and unnatural amino acids, linked together by peptide or amide bonds and each instance of AA may be the same or different than each other instance;

PS is a sulfated or non-sulfated polysaccharide chain comprising one or more monosaccharide units connected by glycosidic linkages; and 'a' is a number from 1 to 10, 'c' is a number from 1 to 100, and each of 'm' and 'n' are independently a number from 1 to 3.

2. The method according to claim 1, wherein the aqueous buffer comprises a phosphate buffering agent.

3. The method according to claim 1, wherein the aqueous buffer is phosphate buffered saline (PBS).

4. The method according to claim 1, wherein the sample of plasma is diluted with the aqueous buffer in a dilution ratio (v/v) of from 1:5 to 1:1000 (sample:buffer).

5. The method according to claim 1, wherein the fluorescent compound is

[Chemical structure: compound with two serine residues linked via amide bonds to a diamino-pyrazine dicarboxamide core]

or a pharmaceutically acceptable salt thereof.

6. The method according to claim 1, wherein the sample of plasma exhibits signs of blood hemolysis.

7. The method according to claim 1, wherein the sample of plasma comes from a human, an animal or an in vitro study.

8. The method according to claim 1, wherein the method further comprises preparing a linear calibration curve for HPLC analysis of the sample of plasma, the linear calibration curve prepared using calibration standards containing the fluorescent compound in a concentration of from 0.4 ng/mL to 400 ng/mL, and wherein the diluted sample analyzed by HPLC comprises the fluorescent compound in a concentration of from 0.4 ng/mL to 400 ng/mL.

9. The method according to claim 8, wherein the diluted sample analyzed by HPLC comprises the fluorescent compound in a concentration of 0.4 ng/mL, and wherein the fluorescent compound is detected with a signal to noise ratio greater than 15:1.

10. A method for measuring the amount of a fluorescent compound in plasma, the method comprising:

diluting a sample of plasma comprising the fluorescent compound with an aqueous buffer comprising a phosphate buffering agent, wherein the sample of plasma is diluted with the aqueous buffer in a dilution ratio (v/v) of from 1:5 to 1:1000 (sample:buffer); and analyzing the diluted sample by high performance liquid chromatography (HPLC) thereby measuring the amount of the fluorescent compound in the sample of plasma;

wherein the sample of plasma is not dried before HPLC analysis, and no internal standard is added to the sample, wherein the method does not include a protein precipitation step that comprises causing proteins to precipitate from the sample of plasma and removing the precipitated proteins from the sample prior to HPLC analysis, wherein the fluorescent compound is a compound of Formula I, or a pharmaceutically acceptable salt thereof, wherein Formula I

[Chemical structure of Formula I: pyrazine ring with substituents $X^1$, $X^2$, $Y^1$, $Y^2$]

each of $X^1$ and $X^2$ is independently —$CO_2R^1$, —$CONR^1R^2$, —CO(AA) or —CONH(PS);

each of $Y^1$ and $Y^2$ is independently selected from the group consisting of —$NR^1R^2$; and $$-\text{N} \begin{array}{c} (CH_2)_m \\ \diagdown \\ \diagup \\ (CH_2)_n \end{array} Z^1;$$

$Z^1$ is a single bond, —$CR^1R^2$—, —O—, —$NR^1$—, —$NCOR^1$—, —S—, —SO—, or —$SO_2$—;

each of $R^1$ to $R^2$ are independently selected from the group consisting of H, —$CH_2(CHOH)_aH$, —$CH_2(CHOH)_aCH_3$, —$CH_2(CHOH)_aCO_2H$, —$(CHCO_2H)_aCO_2H$, —$(CH_2CH_2O)_cH$, —$(CH_2CH_2O)_cCH_3$, —$(CH_2)_aSO_3H$, —$(CH_2)_aSO_3^-$, —$(CH_2)_aSO_2H$, —$(CH_2)_aSO_2^-$, —$(CH_2)_aNHSO_3H$, —$(CH_2)_aNHSO_3^-$, —$(CH_2)_aNHSO_2H$, —$(CH_2)_aNHSO_2^-$, —$(CH_2)_aPO_3H_2$, —$(CH_2)_aPO_3H^-$, and —$(CH_2)_aPO_3^{2-}$;

AA is a peptide chain comprising one or more amino acids selected from the group consisting of natural and unnatural amino acids, linked together by peptide or amide bonds and each instance of AA may be the same or different than each other instance;

PS is a sulfated or non-sulfated polysaccharide chain comprising one or more monosaccharide units connected by glycosidic linkages; and 'a' is a number from 1 to 10, 'c' is a number from 1 to 100, and each of 'm' and 'n' are independently a number from 1 to 3.

11. The method according to claim 10, wherein the fluorescent compound is

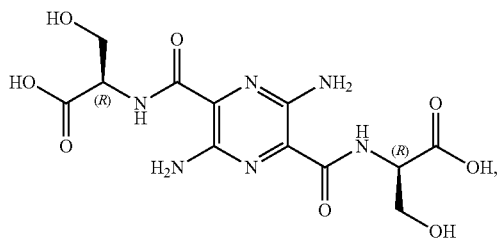

or a pharmaceutically acceptable salt thereof.

12. The method according to claim 10, wherein the aqueous buffer is phosphate buffered saline (PBS).

13. The method according to claim 10, wherein the sample of plasma exhibits signs of blood hemolysis.

14. The method according to claim 10, wherein the sample of plasma comes from a human, an animal or an in vitro study.

15. The method according to claim 10, wherein the sample of plasma comes from a human.

16. The method according to claim 10, wherein the sample of plasma is diluted with the aqueous buffer in a dilution ratio (v/v) of 1:25, 1:30, 1:35, 1:40, 1:45, 1:50, 1:60, 1:70, 1:80, 1:90, 1:100, 1:200, 1:300, 1:400, 1:500, 1:600, 1:700, 1:800, 1:900, or 1:1000 (sample:buffer).

17. The method according to claim 10, wherein the sample of plasma is diluted with the aqueous buffer in a dilution ratio (v/v) of 1:100 (sample:buffer).

18. The method according to claim 10, wherein the aqueous buffer does not cause decomposition of the diluted sample during HPLC analysis.

19. The method according to claim 10, wherein the method further comprises preparing a linear calibration curve for HPLC analysis of the sample of plasma, the linear calibration curve prepared using calibration standards containing the fluorescent compound in a concentration of from 0.4 ng/mL to 400 ng/mL, and wherein the diluted sample analyzed by HPLC comprises the fluorescent compound in a concentration of from 0.4 ng/mL to 400 ng/mL.

20. The method according to claim 19, wherein the diluted sample analyzed by HPLC comprises the fluorescent compound in a concentration of 0.4 ng/mL, and wherein the fluorescent compound is detected with a signal to noise ratio greater than 15:1.

21. The method according to claim 10, wherein the pH of the diluted sample is between about 7.0 and about 7.4.

22. The method according to claim 10, wherein plasma proteins in the diluted sample do not have a peak eluted during HPLC analysis that interferes with a peak of the fluorescent compound eluted during the HPLC analysis.

23. The method according to claim 10, wherein diluting the sample of plasma includes a single diluting step.

* * * * *